(12) United States Patent
Jin et al.

(10) Patent No.: US 10,030,066 B2
(45) Date of Patent: Jul. 24, 2018

(54) IMMUNE RECEPTOR MODIFIER CONJUGATE AND PREPARATION METHOD AND USE THEREOF, COUPLING PRECURSOR FOR PREPARING SAME, AND COMPOUND FOR SYNTHESIZING COUPLING PRECURSOR

(71) Applicants: Shenzhen University, Guangdong (CN); Shenzhen Kangjuzheng Pharmaceutical Technology Co., Ltd, Guangdong (CN)

(72) Inventors: Guangyi Jin, Guangdong (CN); Zhulin Wang, Guangdong (CN)

(73) Assignees: SHENZHEN UNIVERSITY, Shenzhen (CN); SHENZHEN KANGJUZHENG PHARMACEUTICAL TECHNOLOGY CO., LTD, Shenzhen (CN)

( * ) Notice: Subject to any disclaimer, the term of this patent is extended or adjusted under 35 U.S.C. 154(b) by 309 days.

(21) Appl. No.: 14/434,743

(22) PCT Filed: Jun. 26, 2013

(86) PCT No.: PCT/CN2013/077972
§ 371 (c)(1),
(2) Date: Apr. 9, 2015

(87) PCT Pub. No.: WO2014/056333
PCT Pub. Date: Apr. 17, 2014

(65) Prior Publication Data
US 2015/0284445 A1    Oct. 8, 2015

(30) Foreign Application Priority Data
Oct. 10, 2012 (CN) .......................... 2012 1 0382202

(51) Int. Cl.
| | | |
|---|---|---|
| A61K 31/00 | (2006.01) | |
| A61K 47/50 | (2017.01) | |
| C07K 14/705 | (2006.01) | |
| A61K 39/00 | (2006.01) | |
| A61K 39/145 | (2006.01) | |
| A61K 39/39 | (2006.01) | |
| C07D 473/18 | (2006.01) | |
| A61K 47/48 | (2006.01) | |
| A61K 39/12 | (2006.01) | |
| C07K 14/47 | (2006.01) | |

(52) U.S. Cl.
CPC .... C07K 14/70596 (2013.01); A61K 39/0011 (2013.01); A61K 39/12 (2013.01); A61K 39/145 (2013.01); A61K 39/39 (2013.01); A61K 47/481 (2013.01); A61K 47/48246 (2013.01); A61K 47/48338 (2013.01); C07D 473/18 (2013.01); C07K 14/4727 (2013.01); A61K 2039/55511 (2013.01)

(58) Field of Classification Search
None
See application file for complete search history.

(56) References Cited

U.S. PATENT DOCUMENTS

| | | | | |
|---|---|---|---|---|
| 2012/0083473 | A1* | 4/2012 | Holldack | A61K 31/52 514/150 |
| 2012/0231023 | A1* | 9/2012 | Zurawski | C07K 16/2851 424/178.1 |

FOREIGN PATENT DOCUMENTS

| | | |
|---|---|---|
| CN | 101230064 A | 7/2008 |
| CN | 101239980 A | 8/2008 |
| CN | 102439011 A | 5/2012 |
| CN | 102993265 A | 3/2013 |
| EP | 1939202 A1 | 7/2008 |
| EP | 2133353 A1 | 12/2009 |
| WO | 2009005687 A1 | 1/2009 |
| WO | 2010093436 A2 | 8/2010 |
| WO | 2011134669 A1 | 11/2011 |
| WO | 2012038058 A1 | 3/2012 |

OTHER PUBLICATIONS

Scharma et al. ("Scharma", Drug Discover, 2006, 5, 147-159).*
Shi et al. ("Shi", Cancer bio & Therapy, 2005, 4, 218-224).*
Davis et al. ("Davis", PNAS, 2005, 102, 5981-5986).*
Bostwick, D., et al., "Prostate Specific Membrane Antigen Expression in Prostatic Intraepithelial Neoplasia and Adenocarcinoma", "Cancer", Jun. 1, 1998, pp. 2256-2261, vol. 82, No. 11.
Brahmer, J., et al., "Safety and Activity of AntiPD-L1 Antibody in Patients with Advanced Cancer", "N Engl J Med", Jun. 28, 2012, pp. 2455-2465, vol. 366, No. 26.
Cai, H., et al., "Synthesis of Tn/T Antigen MUC1 Glycopeptide BSA Conjugates and Their Evaluation as Vaccines", "Eur. J. Org. Chem.", May 2, 2011, pp. 3685-3689.
Cai, H., et al., "Towards a Fully Synthetic MUC1-Based Anticancer Vaccine: Efficient Conjugation of Glycopeptides with Mono-, Di-, and Tetravalent Lipopeptides Using Click Chemistry", "Chem. Eur. J.", Apr. 27, 2011, pp. 6396-6406, vol. 17.

(Continued)

*Primary Examiner* — Misook Yu
*Assistant Examiner* — Kauser M Akhoon
(74) *Attorney, Agent, or Firm* — Hultquist, PLLC; Steven J. Hultquist

(57) ABSTRACT

Disclosed is an immune receptor modifier conjugate, obtained from the reaction between a coupling precursor and a biotic ligand, the coupling precursor being a 9-position aminomethyl benzyl purine biotic coupling precursor, and the biotic ligand being selected from one or more of polypeptide, protein, glycoprotein, polysaccharide, polynucleotide, inactivated cells and inactivated microbes. The immune receptor modifier couplet can be used for immunomodulation, antibody preparation, anti-virus, diabetes, tumor immunomodulation, and tumor bio-immunotherapy. The conjugate compounds or salts thereof can be prepared into various therapeutic drugs, and can be prepared into a compound drug together with other drugs, or pharmaceutically acceptable carrier composites or conjugates. Also disclosed are compounds for synthesizing the coupling precursor and salts thereof.

7 Claims, 5 Drawing Sheets

(56) References Cited

OTHER PUBLICATIONS

Chao, M., et al., "Calreticulin is the dominant pro-phagocytic signal on multiple human cancers and is counterbalanced by CD47", "Sci Transl Med.", Dec. 22, 2010, pp. 63ra94, 1-21, vol. 2, No. 63.

Cheever, M., et al., "The Prioritization of Cancer Antigens: A National Cancer Institute Pilot Project for the Acceleration of Translational Research", "Clin Cancer Res", Sep. 1, 2009, pp. 5323-5337, vol. 15, No. 17.

Chen, Y., et al., "Advances in the studies of transcription factor Sox2", "Chinese Bulletin of Life Sciences", Jun. 2004, pp. 129-134 (English Abstract), vol. 16, No. 3.

Chen, T., et al., "Construction and identification of eukaryotic expression vector of mouse Oct4 gene", "Progress in Modern Biomedicine", May 2010, pp. 1610-1612 (English Abstract), vol. 10, No. 9.

Chiriva-Internati, M., et al., "Cancer Testis Antigen Vaccination Affords Long-Term Protection in a Murine Model of Ovarian Cancer", "PLoS One", May 12, 2010, pp. e10471, 1-13, vol. 5, No. 5.

Hatakeyama, S., et al., "Targeted drug delivery to tumor vasculature by a carbohydrate mimetic peptide", "PNAS", Dec. 6, 2011, pp. 19587-19592, vol. 108, No. 49.

Kaiser, A., et al., "Fully Synthetic Vaccines Consisting of Tumor-Associated MUC1 Glycopeptides and a Lipopeptide Ligand of the Toll-like Receptor 2", "Angew. Chem. Int. Ed.", Apr. 1, 2010, pp. 3688-3692, vol. 49.

Kastenmueller, K., et al., "Protective T cell immunity in mice following protein-TLR7/8 agonist-conjugate immunization requires aggregation, type I IFN, and multiple DC subsets", "The Journal of Clinical Investigation", May 2011, pp. 1782-1796, vol. 121, No. 5.

Kelber, J., et al., "KRas Induces a Src/PEAK1/ErbB2 Kinase Amplification Loop That Drives Metastatic Growth and Therapy Resistance in Pancreatic Cancer", "Cancer Res.", May 15, 2012, pp. 2554-2564, vol. 72, No. 10.

Lakshminarayanan, V., et al., "Immune recognition of tumor-associated mucin MUC1 is achieved by a fully synthetic aberrantly glycosylated MUC1 tripartite vaccine", "PNAS", Jan. 3, 2012, pp. 261-266, vol. 109, No. 1.

Li, W., et al., "Expression of PSMA gene and protein in prostate cancer", "Acta Univ Med Nanjing", Nov. 2010, pp. 1608-1611 (English Abstract), vol. 30, No. 11.

Li, J., et al., "Expression of periostin and its clinicopathological relevance in gastric cancer", "World J Gastroenterol", Oct. 21, 2007, pp. 5261-5266, vol. 13, No. 39.

Malanchi, I., et al., "Interactions between cancer stem cells and their niche govern metastatic colonization", "Nature", Jan. 5, 2012, pp. 85-89, vol. 481.

Ni, X., et al., "Structure and function of annexin A1 and its relationship with malignant tumor", "Oncology Progress", Jan. 2010, pp. 63-66, vol. 8, No. 1.

Ni, X., et al., "Structure and function of annexin A1 and its relationship with malignant tumor", "Oncology Progress", Jan. 2010, pp. 63-66 (English Abstract), vol. 8, No. 1.

Shi, R., et al., "In vitro cytotoxity and reversal effects of PH II-7 in human multidrug-resistant breast cancer MCF-7/ADR cells", "China Oncology", 2010, pp. 321-326 (English Abstract), vol. 20, No. 5.

Song, L., et al., "Detection of Serum gastric carcinoma associated antigen MG7-Ag is valuable in diagnosis of gastric carcinoma", "China Oncology", 2010, pp. 312-313, vol. 20, No. 4.

Song, L., et al., "Detection of Serum gastric carcinoma associated antigen MG7-Ag is valuable in diagnosis of gastric carcinoma", "China Oncology", 2010, pp. 312-313 (English Abstract), vol. 20, No. 4.

Wang, M., et al., "Cloning of human sperm protein (SP17) and expression in *Escherichia coli* DH5alpha", "Chinese Journal of Pathophysiology", 2001, pp. 1019-1021 (English Abstract), vol. 17, No. 10.

Wang, S., et al., "Effect of hepatitis B vaccine with CpG oligodeoxynucleotide or Bacilli Calmette Guerin on immune responses in mice", "World Chin J Digestol", Sep. 15, 2005, pp. 2078-2081 (English Abstract), vol. 13, No. 17.

Wang, S., et al., "The development in the study about the functions of Twist and Akt in malignant tumor", "Journal of Shenyang Medical College", Sep. 2010, pp. 182-184, vol. 12, No. 3.

Wang, S., et al., "The development in the study about the functions of Twist and Akt in malignant tumor", "Journal of Shenyang Medical College", Sep. 2010, pp. 182-184 (English Abstract), vol. 12, No. 3.

Weeratna, R., et al., "TLR agonists as vaccine adjuvants: comparison of CpG ODN and Resiquimod (R-848)", "Vaccine", Jul. 18, 2005, pp. 5263-5270, vol. 23.

Wilkinson, B., et al., "Self-Adjuvanting Multicomponent Cancer Vaccine Candidates Combining Per-Glycosylated MUC1 Glycopeptides and the Toll-like Receptor 2 Agonist Pam3CysSer", "Angew. Chem. Int. Ed.", Jan. 7, 2011, p. 1635 1639, vol. 50.

Yang, J., et al., "Overexpression of HER2 gene and treatment of breast carcinoma", "Med J CASC", Feb. 2002, pp. 69-70, vol. 4, No. 1.

Yang, J., et al., "Overexpression of HER2 gene and treatment of breast carcinoma", "Med J Casc", Feb. 2002, pp. 69-70 (English Abstract), vol. 4, No. 1.

Zhang, X., et al., "Expression of MMP-10 in Lung Cancer", "Anticancer Research", 2007, pp. 2791-2796, vol. 27.

Zhang, Q., et al., "Cloning, expression and purification of human Sox2 gene", "Journal of Huazhong Normal University", Mar. 2008, pp. 102-105 (English Abstract), vol. 42, No. 1.

Zhang, J., et al., "Research the expression of Oct4 in multiple adenocarcinoma", "China Medical Herald", Mar. 2011, pp. 17-19 (English Abstract), vol. 8, No. 8.

Zhou, L., et al., "Advances in the research of sodium-dependent glucose cotransporter 2 inhibitors", "Chinese Journal of Medicinal Chemistry", Aug. 2011, pp. 322-327 (English Abstract), vol. 21, No. 4.

Note: For the non-patent literature citations that no month of publication is indicated, the year of publication is more than 1 year prior to the effective filing date of the present application.

\* cited by examiner

IMMUNE RECEPTOR MODIFIER CONJUGATE AND PREPARATION METHOD AND USE THEREOF, COUPLING PRECURSOR FOR PREPARING SAME, AND COMPOUND FOR SYNTHESIZING COUPLING PRECURSOR

CROSS-REFERENCE TO RELATED APPLICATIONS

This application is a U.S. national phase under the provisions of 35 U.S.C. § 371 of International Patent Application No. PCT/CN13/77972 filed Jun. 26, 2013, which in turn claims priority of Chinese Patent Application No. 201210382202.8 filed Oct. 10, 2012. The disclosures of such international patent application and Chinese priority patent application are hereby incorporated herein by reference in their respective entireties, for all purposes.

FIELD OF THE INVENTION

The present invention relates to an immune receptor modifier conjugate, its preparation and use thereof for anti-tumor, antivirus, diabetes, antibody induction and immunomodulation. In particular, the present invention relates to 9-position aminomethyl benzyl purine biotic coupling precursor for preparing the above-mentioned immune receptor modifier conjugate. In addition, the present invention relates to the compounds or salts thereof for synthesizing the coupling precursor.

BACKGROUND OF THE INVENTION

Improved immunological effect can often be realized by combined application or conjugation of immune agonists and immune antigens such as polypeptides, proteins, glycoproteins, polysaccharides, polynucleotides, cell lysates, inactivated cells and inactivated microorganisms (*World Chin J Digestol* 2005 Sep. 15, 13(17):2078-2081; *Vaccine*, Volume 23, Issue 45, 1 Nov. 2005, Pages 5263-5270; *The J. Clin. Invest.* 2011, 121(5), 1782-1796).

The present invention prepares a series of small molecular immune agonist coupling precursors and conjugates synthesized from such immune agonist coupling precursors with biotic ligands or immune antigens. Also disclosed are the uses of such conjugates for anti-tumor, anti-virus, diabetes, antibody induction and immunomodulation.

SUMMARY OF THE INVENTION

The purpose of the present invention is to provide an immune receptor modifier conjugate with enhanced immunological effect and the preparation method thereof. The purpose of the present invention is to provide a coupling precursor for preparing such conjugate and to provide compounds or salts thereof for synthesizing such coupling precursor. A further purpose of the present invention is to provide the use of such immune receptor modifier conjugate in immunomodulation, antibody preparation, anti-virus, diabetes, tumor immunomodulation and tumor biological-immunotherapy.

According to one aspect of the present invention, provided is an immune receptor modifier conjugate which is obtained by reacting a coupling precursor with a biotic ligand, wherein the conjugate is a compound of general formula (I):

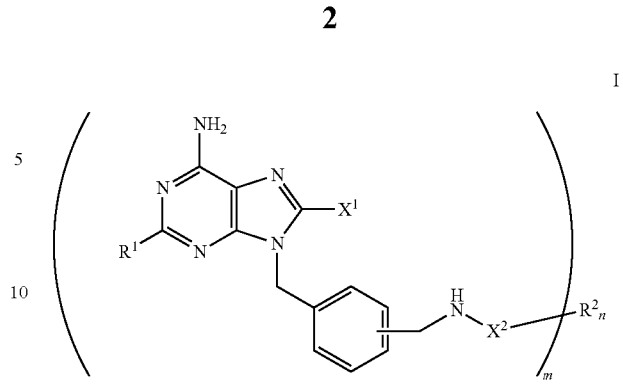

wherein $R^2$ represents the biotic ligand, $X^1$ represents OH or SH, $R^1$ represents linear alkyl, branched alkyl, substituted alkyl, unsubstituted alkyl or alkoxyalkyl, $X^2$ represents a coupling group; m and n each are an integer selected from 1 to 10, m is the number of small molecular agonist (m is defined as coupling degree), and n is the number of the biotic ligand.

When the coupling precursor is a compound of formula 1:

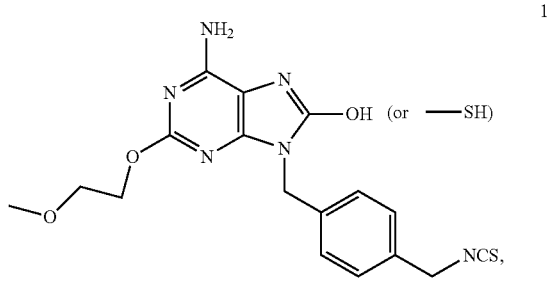

$X^2$ represents the group thiocarbonyl

When the coupling precursor is a compound of formula 2:

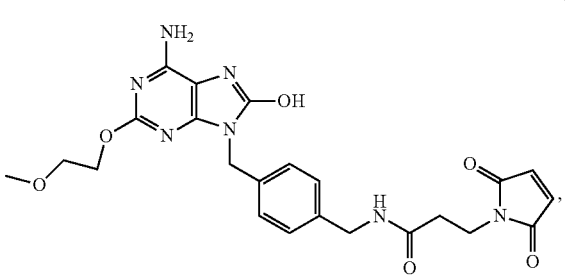

$X^2$ represents the group

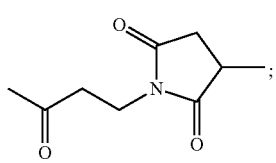

When the coupling precursor is a compound of formula 3:

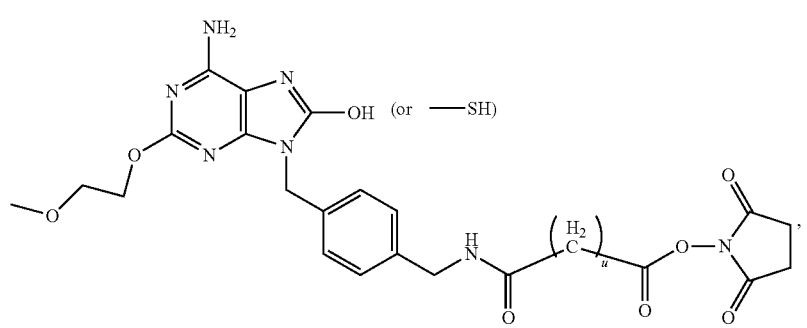

$X^2$ represents the group

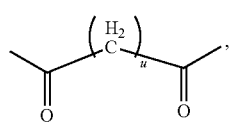

in which u is an integers selected from 0 to 12; and
When the coupling precursor is a compound of formula (4):

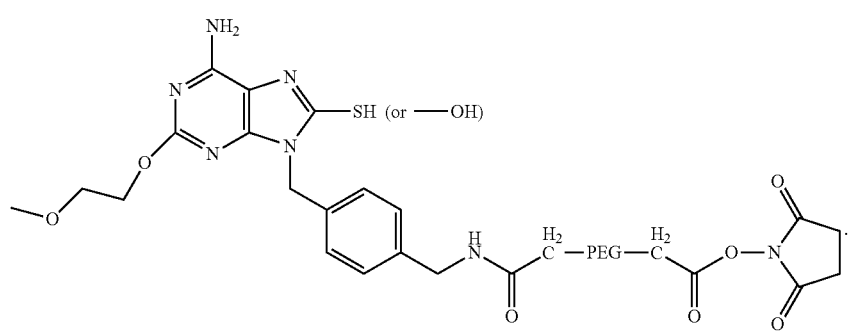

$X^2$ represents the group

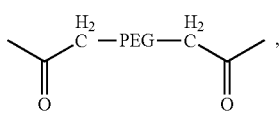

in which PEG represents a polyethylene glycol group.

Among the above-mentioned immune receptor modifier conjugates, the biotic ligand is one or more selected from polypeptide, protein, glycoprotein, polysaccharide, polynucleotide, inactivated cells and inactivated microorganisms.

Among the above mentioned immune receptor modifier conjugates, PEG is a polyethylene glycol group

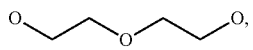

such as a di-polyethylene glycol group $$\text{O}\smile\text{O}\smile\text{O},$$

a tri-polyethylene glycol group $$\text{O}\smile\text{O}\smile\text{O}\smile\text{O},$$

and a tetra-polyethylene glycol group $$\text{O}\smile\text{O}\smile\text{O}\smile\text{O}\smile\text{O},$$

When the coupling precursor is a compound of formula 3 or 4, by using the biotic ligand $R^2$, such as OCT4, SOX2, NANOG, MUC1, MG7, POSTN, Twist, Anxa1, Akt, CD47, Sp17, PSMA, M2e (monomer and tetramer), $NP_{366\text{-}374}$ (9-peptide epitope), FOXO1, PEAK1, HER2, MMP-10, PD-L1, PD-1, and SGLT2, the typical representative structures of the protein conjugates formed are as follows:

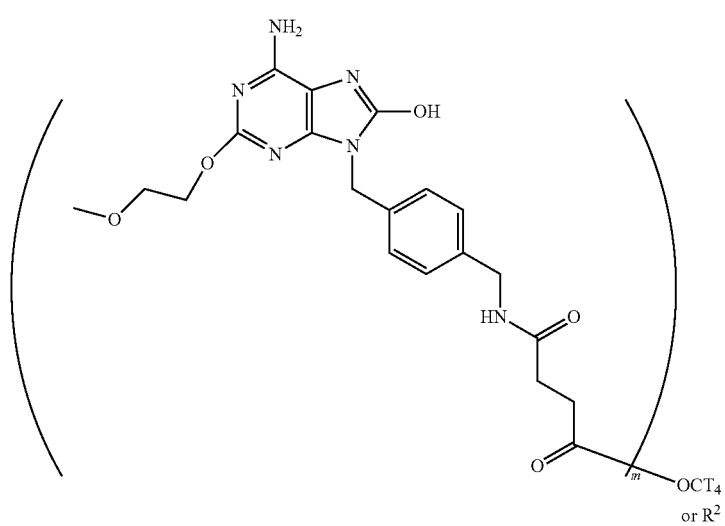

5

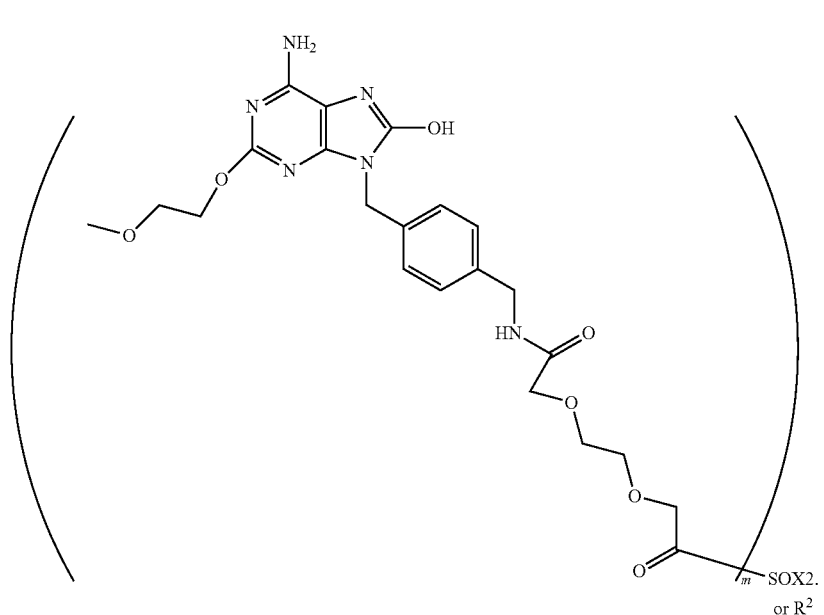

6

In formulae (5) and (6), the expression "or R²" means that OCT4 and SOX2 can be substituted by other antigens, proteins or polypeptides, wherein the substitution by NANOG results in compounds 5-3 and 6-3 respectively; the substitution by MUC1 results in compounds 5-4 and 6-4 respectively; the substitution by MG7 results in compounds 5-5 and 6-5 respectively; the substitution by POSTN results in compounds 5-6 and 6-6 respectively; the substitution by Twist results in compounds 5-7 and 6-7 respectively; the substitution by Anxa1 results in compounds 5-8 and 6-8 respectively; the substitution by Akt results in compounds 5-9 and 6-9 respectively; the substitution by CD47 results in compounds 5-10 and 6-10 respectively; the substitution by Sp17 results in compounds 5-11 and 6-11 respectively; the substitution by PSMA results in compounds 5-12 and 6-12 respectively; the substitution by M2e (monomer and tetramer) results in compounds 5-13 and 6-13 respectively; the substitution by $NP_{366-374}$ (9-peptide epitope) results in compounds 5-14 and 6-14 respectively; the substitution by SGLT2 results in compounds 5-15 and 6-15 respectively; the substitution by PEAK1 results in compounds 5-16 and 6-16 respectively; the substitution by HER2 results in compounds 5-17 and 6-17 respectively; the substitution by MMP-10 results in compounds 5-18 and 6-18 respectively; the substitution by PD-L1 results in compounds 5-19 and 6-19 respectively; and the substitution by PD-1 results in compounds 5-20 and 6-20 respectively.

The aforementioned compounds are shown in tables 1 and 2 below:

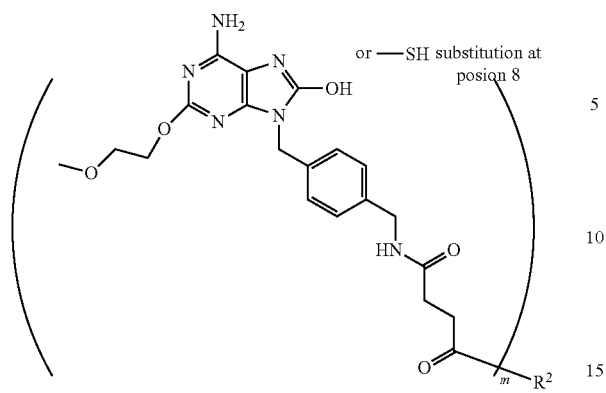
Conjugate 5-3 - 5-19
TABLE 1
Conjugates formed by the coupling precursor of formula 3 and various biotic ligands
| $R^2$ | NANOG | MUC1 (epitope) | MG7 | POSTN | Twist | Anxa1 | Akt | CD47 | Sp17 |
|---|---|---|---|---|---|---|---|---|---|
| Conjugate | 5-3 | 5-4 | 5-5 | 5-6 | 5-7 | 5-8 | 5-9 | 5-10 | 5-11 |
| $R^2$ | PSMA | M2e | $NP_{366\text{-}374}$ | SGLT2 | PEAK1 | HER2 | MMP-10 | PD-L1 | PD-1 |
| Conjugate | 5-12 | 5-13 | 5-14 | 5-15 | 5-16 | 5-17 | 5-18 | 5-19 | 5-20 |
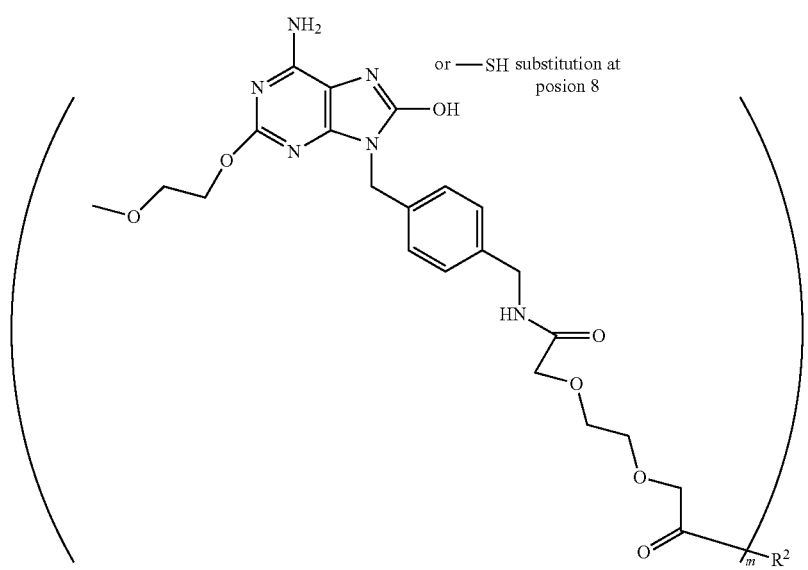
Conjugate 6-3 - 6-19

TABLE 2

Conjugates formed by the coupling precursor of formula (4) and various biotic ligands

| $R^2$ | NANOG | MUC1 (epitope) | MG7 | POSTN | Twist | Anxa1 | Akt | CD47 | Sp17 |
|---|---|---|---|---|---|---|---|---|---|
| Conjugate | 6-3 | 6-4 | 6-5 | 6-6 | 6-7 | 6-8 | 6-9 | 6-10 | 6-11 |
| $R^2$ | PSMA | M2e | $NP_{366-374}$ | SGLT2 | PEAK1 | HER2 | MMP-10 | PD-L1 | PD-1 |
| Conjugate | 6-12 | 6-13 | 6-14 | 6-15 | 6-16 | 6-17 | 6-18 | 6-19 | 6-20 |

Among them, OCT4, SOX2 and NANOG are tumor stem cell antigen proteins (*Chinese Medicine Herald*, 2011, 8(8): 17-20; *Chinese Bulletin of Life Sciences*, 2004, 16(3):129-134); MG7 is a stomach cancer-related antigen protein (*China Oncology*, 2010, 20(4): 312-313); MUC1 is an antigen related to various tumors (*European Journal of Organic Chemistry*, 2011, 20(21): 3685-3689); POSTN is a tumor-related protein (*Nature*, 2012, 481: 85-89); Twist and Akt are both tumor-related antigens (*Journal of Shenyang Medical College*, 2010, 12(3): 182-184); Anxa1 is specifically expressed in various tumor tissues (*PNAS*, 2011, Oct. 3, 19587-19592; *Oncology Progress*, 2010, Jan. 8(1):63-66); CD47 is highly expressed on the surface of almost every type of cancer cells (*Science: Translational Medicine*, 22 Dec. 2010, Vol 2, Issue 63 63ra94); Sp17 is a tumor antigen having very high expression in ovarian carcinoma cells (*PloS ONE*, 2010, 5(5), e10471, 1-13); PSMA is a special biomarker of prostate cancer (*Cancer*, 1998, 82(11): 2256-2261); M2e and $NP_{366-374}$ are epitope polypeptides in the conserved protein of influenza virus A; SGLT2 is a functional protein related to sugar metabolism (*Chinese Journal of Medicinal Chemistry*, 2011, Vol. 21, No. 4, p 322); PEAK1 is a biomarker of early pancreatic cancer (*Cancer Res.* 2012 May 15; 72(10):2554-64); HER2 is a proto-oncogene human epidermal growth factor receptor 2 (*MEDICAL JOURNAL OF CASC*, 2002, 4 (1), 69-70); MMP-10 is a protein closely related to the occurrence and metastasis of lung carcinoma (*Anticancer Res.* 2007 July-August; 27(4C): 2791-5); and PD-L1 and PD-1 are a ligand and a receptor of tumor immune escape, respectively (*N. Engl. J. Med.*, 2012, Jun. 2, 1-11).

When the coupling precursor is a compound of formula 1 or 2, typical representative synthesis and structure formulae of the polypeptide conjugates formed from the coupling precursor and biotic ligand $R^2$ (such as MUC1

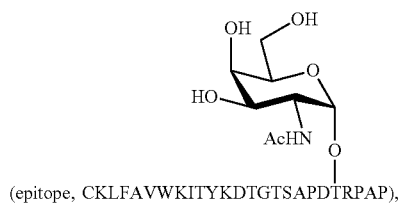

(epitope, CKLFAVWKITYKDTGTSAPDTRPAP),

MG7 and M2e (monomer)) are as follows:

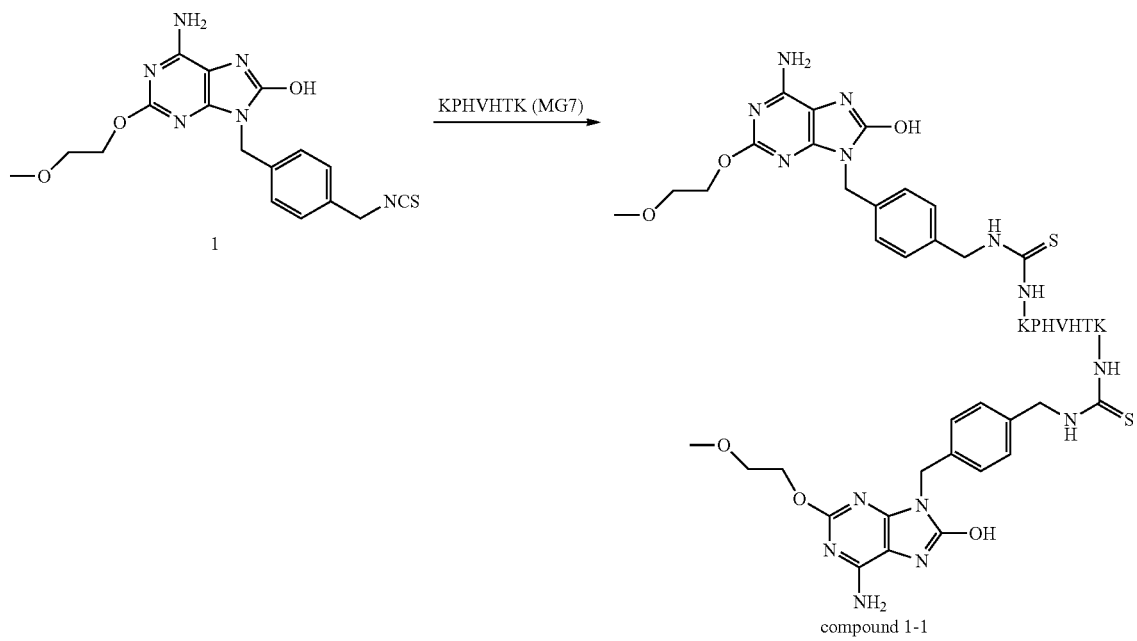

compound 1-1

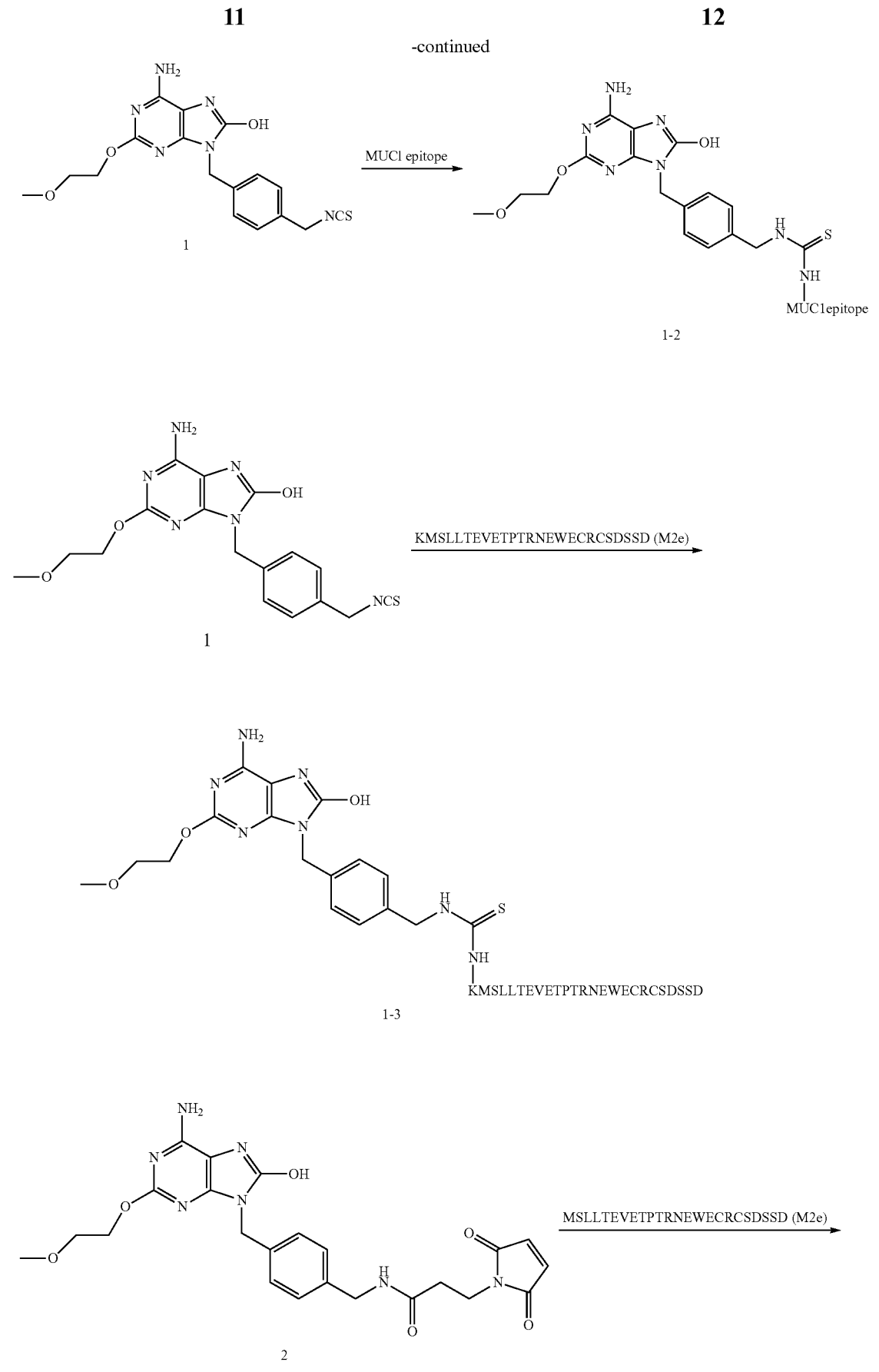

-continued

-continued
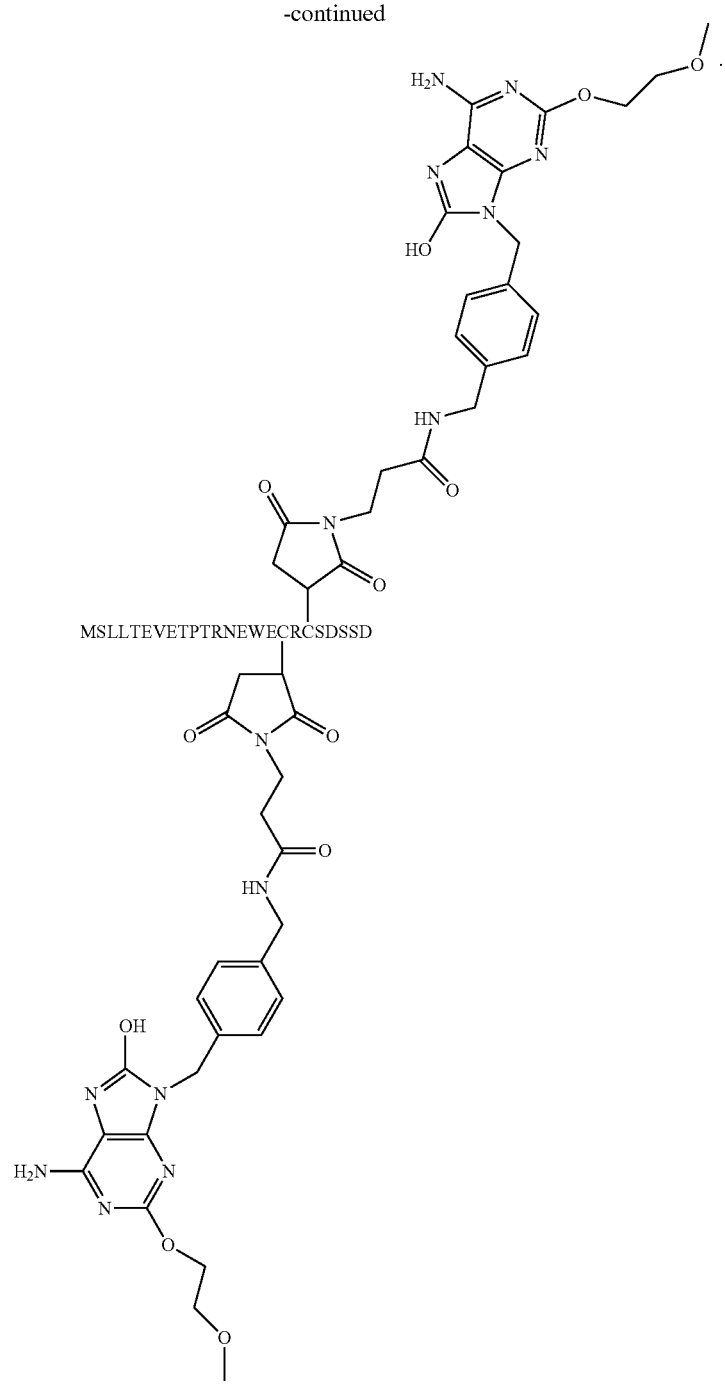
compound 2-1
For the immune receptor modifier conjugates of this invention, suitable biotic ligands are not limited to the polypeptides or proteins as listed above, and can also be the tumor antigens as shown is table 3.

TABLE 3

Suitable biotic ligands in the form of tumor antigens

| Serial No. | 1 | 2 | 3 | 4 | 5 | 6 | 7 | 8 | 9 |
|---|---|---|---|---|---|---|---|---|---|
| Antigen | WT1 | MUC2 | LMP2 | HPV E6 E7 | EGFR,III | HER-2/neu | Idiotype | MAGE A3 | p53 monmutant |
| Percentage of positive expression and cells (0.07) | 0.37 | 1.0 | 0.37 | 0.23 | 0.37 | 0.37 | 1.0 | 0.37 | 0.37 |
| Stem cell performance (0.04) | 1.0 | 1.0 | 1.0 | 0.73 | 1.0 | 0.66 | 0.66 | 1.0 | 1.0 |
| Number of parents with cancer cell antigen (0.04) | 1.0 | 1.0 | 1.0 | 0.16 | 0.11 | 0.11 | 0.14 | 1.0 | 1.0 |
| Amount of antigen (0.04) | 1.0 | 1.0 | 1.0 | 0.13 | 1.0 | 1.0 | 1.0 | 1.0 | 1.0 |
| Constitutive expression in cells (0.02) | 0.95 | 0.25 | 0.95 | 0.95 | 1.0 | 0.25 | 1.0 | 0.95 | 0.95 |

| Serial No. | 10 | 11 | 12 | 13 | 14 | 15 | 16 | 17 | 18 |
|---|---|---|---|---|---|---|---|---|---|
| Antigen | NY-ESO-1 | PSMA | GD2 | CEA | MelanA/V MART1 | Ras Mutant | Gp100 | P53 mutant | Proteinase3 (PR1) |
| Percentage of positive expression and cells (0.07) | 0.37 | 1.0 | 1.0 | 0.37 | 0.37 | 0.23 | 0.37 | 1.0 | 0.37 |
| Stem cell performance (0.04) | 1.0 | 0.2 | 0.2 | 0.66 | 0.2 | 1.0 | 0.2 | 0.77 | 0.2 |
| Number of parents with cancer cell antigen (0.04) | 0.11 | 1.0 | 1.0 | 1.0 | 1.0 | 0.16 | 1.0 | 0.14 | 1.0 |
| Amount of antigen (0.04) | 1.0 | 1.0 | 1.0 | 1.0 | 1.0 | 0.13 | 1.0 | 0.13 | 0.13 |
| Constitutive expression in cells (0.02) | 0.95 | 1.0 | 0.62 | 0.25 | 0.95 | 0.95 | 0.95 | 0.95 | 0.95 |

| Serial No. | 19 | 20 | 21 | 22 | 23 | 24 | 25 | 26 | 27 |
|---|---|---|---|---|---|---|---|---|---|
| Antigen | Bct-abo | Tyrosinase | Survivin | PSA | hTERT | Sarcocna translocation breakpoints | EphA2 | PAP | ML-IAP |
| Percentage of positive expression and cells (0.07) | 0.23 | 0.37 | 0.37 | 0.08 | 0.23 | 1.0 | 0.37 | 0.23 | 0.37 |
| Stem cell performance (0.04) | 1.0 | 0.2 | 0.66 | 0.66 | 1.0 | 1.0 | 0.2 | 0.2 | 0.2 |
| Number of parents with cancer cell antigen (0.04) | 0.16 | 1.0 | 1.0 | 0.16 | 0.16 | 1.0 | 1.0 | 0.16 | 1.0 |
| Amount of antigen (0.04) | 0.13 | 1.0 | 1.0 | 1.0 | 1.0 | 0.13 | 1.0 | 1.0 | 1.0 |
| Constitutive expression in cells (0.02) | 0.95 | 0.95 | 0.95 | 0.95 | 0.25 | 0.95 | 0.95 | 1.0 | 0.25 |

| Serial No. | 28 | 29 | 30 | 31 | 32 | 33 | 34 | 35 | 36 |
|---|---|---|---|---|---|---|---|---|---|
| Antigen | AFP | EpCAM | ERG(TMR PSS2 ETS fusion gene) | NA17 | PAX3 | ALK | Androgen receptor | Cyclin B1 | Polysialic |
| Percentage of positive expression and cells (0.07) | 0.37 | 1.0 | 0.37 | 0.00 | 0.08 | 1.0 | 0.37 | 0.32 | 1.0 |
| Stem cell performance (0.04) | 1.0 | 1.0 | 0.66 | 0.00 | 0.2 | 1.0 | 0.66 | 0.66 | 0.2 |
| Number of parents with cancer cell antigen (0.04) | 1.0 | 1.0 | 1.0 | 1.0 | 1.0 | 1.0 | 1.0 | 1.0 | 1.0 |
| Amount of antigen (0.04) | 1.0 | 1.0 | 0.13 | 0.13 | 1.0 | 0.27 | 1.0 | 1.0 | 1.0 |
| Constitutive expression in cells (0.02) | 0.25 | 1.0 | 0.95 | 0.95 | 0.95 | 0.95 | 0.95 | 0.95 | 1.0 |

| Serial No. | 37 | 38 | 39 | 40 | 41 | 42 | 43 | 44 | 45 |
|---|---|---|---|---|---|---|---|---|---|
| Antigen | MYCN | Rhoc | TRP-2 | GD3 | Fucosyl GM1 | Medothelin | PSCA | MEGE A1 | sLe(a) |
| Percentage of positive expression and cells (0.07) | 0.37 | 0.37 | 0.37 | 1.0 | 1.0 | 0.37 | 0.37 | 0.00 | 1.0 |
| Stem cell performance (0.04) | 0.2 | 0.66 | 1.0 | 0.2 | 0.2 | 0.66 | 0.2 | 0.2 | 0.2 |
| Number of parents with cancer cell antigen (0.04) | 1.0 | 1.0 | 1.0 | 1.0 | 1.0 | 1.0 | 1.0 | 0.16 | 1.0 |
| Amount of antigen (0.04) | 1.0 | 1.0 | 1.0 | 1.0 | 1.0 | 1.0 | 1.0 | 1.0 | 1.0 |
| Constitutive expression in cells (0.02) | 0.95 | 0.95 | 0.95 | 1.0 | 1.0 | 1.0 | 1.0 | 0.95 | 0.25 |

| Serial No. | 46 | 47 | 48 | 49 | 50 | 51 | 52 | 53 | 54 |
|---|---|---|---|---|---|---|---|---|---|
| Antigen | CYP1B1 | PLAC1 | GM3 | BORIS | Tn | GloboH | ETV6-AML | NY-BR-1 | RGS5 |
| Percentage of positive expression and cells (0.07) | 1.0 | 0.37 | 0.37 | 0.08 | 0.37 | 0.37 | 0.37 | 0.36 | 0.35 |
| Stem cell performance (0.04) | 0.2 | 0.2 | 0.2 | 0.66 | 0.2 | 0.00 | 0.00 | 0.00 | 0.00 |
| Number of parents with cancer cell antigen (0.04) | 1.0 | 0.11 | 1.0 | 0.16 | 1.0 | 1.0 | 0.00 | 0.39 | 1.0 |
| Amount of antigen (0.04) | 1.0 | 1.0 | 1.0 | 1.0 | 1.0 | 0.12 | 1.0 | 0.12 | 0.00 |

TABLE 3-continued

| Suitable biotic ligands in the form of tumor antigens | | | | | | | | | |
|---|---|---|---|---|---|---|---|---|---|
| Constitutive expression in cells (0.02) | 0.95 | 1.0 | 0.25 | 0.95 | 1.0 | 1.35 | 1.0 | 1.0 | 0.35 |

| No. | 55 | 56 | 57 | 58 | 59 | 60 | 61 | 62 | 63 |
|---|---|---|---|---|---|---|---|---|---|
| Antigen | SART3 | STn | Carbonic anhydrase IX | PAX5 | OY-TES1 | Sperm protein 17 | LCK | HMWMAA | AKAP-4 |
| Percentage of positive expression and cells (0.07) | 0.35 | 0.34 | 0.34 | 0.33 | 0.32 | 0.30 | 0.28 | 0.27 | 0.26 |
| Stem cell performance (0.04) | 0.00 | 0.00 | 0.00 | 0.00 | 0.00 | 0.1 | 0.00 | 0.1 | 0.1 |
| Number of parents with cancer cell antigen (0.04) | 1.0 | 1.0 | 1.0 | 0.39 | 0.1 | 0.11 | 1.0 | 0.11 | 0.11 |
| Amount of antigen (0.04) | 0.00 | 0.25 | 0.00 | 1.0 | 1.0 | 0.25 | 0.00 | 0.00 | 0.12 |
| Constitutive expression in cells (0.02) | 0.35 | 0.23 | 0.35 | 0.21 | 0.54 | 0.54 | 0.35 | 0.35 | 0.54 |

| No. | 64 | 65 | 66 | 67 | 68 | 69 | 70 | 71 | 72 |
|---|---|---|---|---|---|---|---|---|---|
| Antigen | SSX2 | XAGE 1 | B7H3 | Legumain | Tie 2 | Page4 | VEGFR2 | MAD-CT-1 | FAP |
| Percentage of positive expression and cells (0.07) | 0.26 | 0.23 | 0.22 | 0.19 | 0.18 | 0.17 | 0.16 | 0.15 | 0.14 |
| Stem cell performance (0.04) | 0.00 | 0.00 | 0.00 | 0.1 | 0.1 | 0.00 | 0.1 | 0.00 | 0.1 |
| Number of parents with cancer cell antigen (0.04) | 0.39 | 0.1 | 0.00 | 0.11 | 0.11 | 0.00 | 0.11 | 0.1 | 0.00 |
| Amount of antigen (0.04) | 0.25 | 0.00 | 0.25 | 0.00 | 0.00 | 0.12 | 0.12 | 0.00 | 0.00 |
| Constitutive expression in cells (0.02) | 0.54 | 0.54 | 0.35 | 0.35 | 0.23 | 0.21 | 0.1 | 0.54 | 0.1 |

| Serial No. | 73 | 74 | 75 |
|---|---|---|---|
| Antigen | PDGFR-b | MAD-CT-2 | Fos-related antigen 1 |
| Percentage of positive expression and cells (0.07) | 0.14 | 0.14 | 0.13 |
| Stem cell performance (0.04) | 0.0 | 0.0 | 0.1 |
| Number of parents with cancer cell antigen (0.04) | 0.11 | 0.1 | 0.11 |
| Amount of antigen (0.04) | 0.12 | 0.00 | 0.00 |
| Constitutive expression in cells (0.02) | 0.1 | 0.54 | 0.1 |

(Characteristic, preparation and source of the tumor antigens as shown in table 2 may be found in *Clin Cancer Res*, 2009; 15(17), 5323-5337).

Preparation of the Coupling Precursor:

Synthesis of Coupling Precursor 1—Synthesis Protocol:

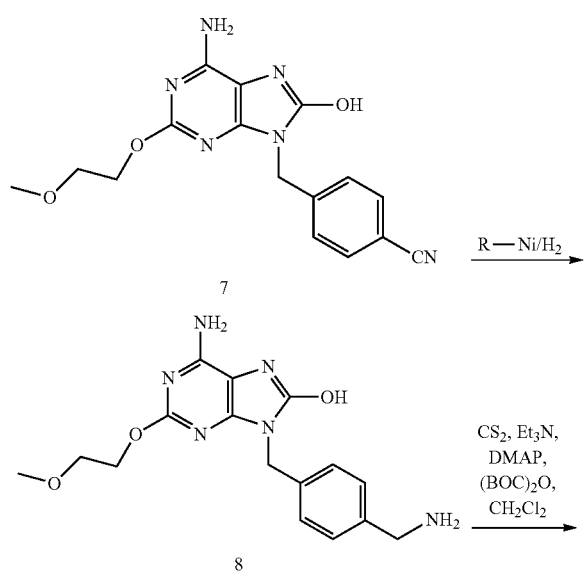

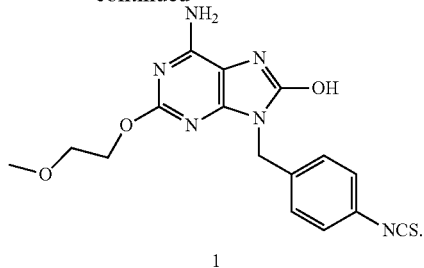

Method for preparing compound of formula 7 is described in WO 2009005687 for compound 1096159-02-2P.

Synthesis Process:

Compound 7 (5 g) was dissolved into methanol (100 ml) and active nickel (0.5 g) was added. The mixture was reduced by hydrogenation at room temperature under 3 atm. for 24 h. After the catalyst nickel was filtered off, the residue was concentrated under reduced pressure to small volume, frozen at −10° C. for 12 h, and precipitated to give a solid product 8 (3 g, yield 60%). Melting point: 265-267° C. MS (ESI, M+1): 345.

Compound 8 (1 g, 2.9 mmol) was mixed with carbon disulfide (2 ml), triethylamine (0.5 ml), DMAP (0.1 g), $(BOC)_2O$ (640 mg) and dichloromethane (50 ml). The mixture was stirred at room temperature for 2 h, heated under reflux for 4 h, concentrated under reduced pressure, and separated by silica gel column chromatography (5% methanol-dichloromethane) to give compound 1 (0.7 g, yield 65%). Melting point: 221-223° C., MS (ESI, M+1): 373.

Synthesis of Coupling Precursor 2—Synthesis Protocol:

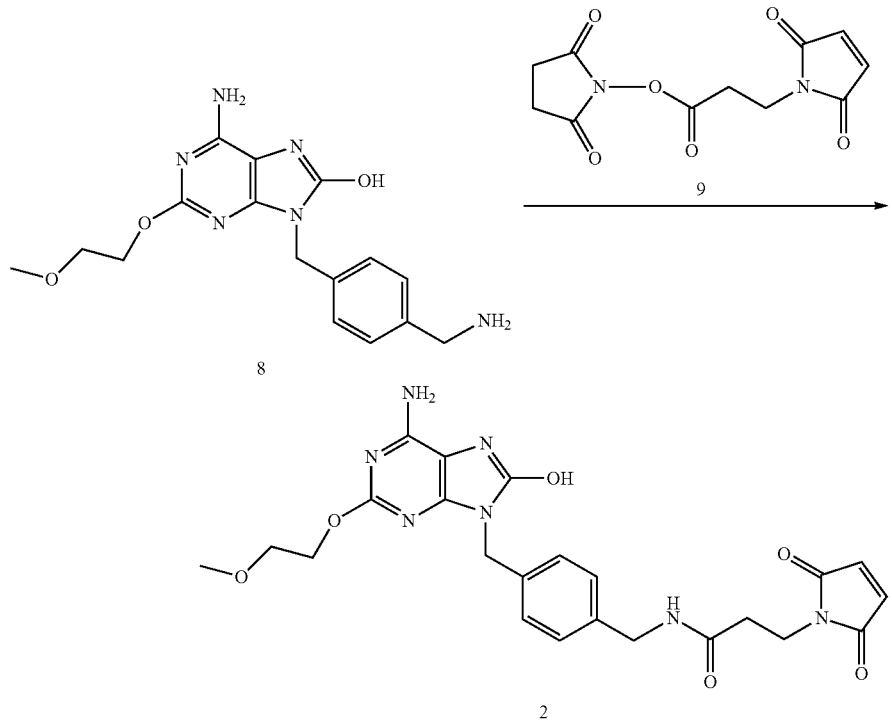

Synthesis Process: Compound 8 (1 g) was mixed with compound 9 (0.78 g) in DMF (30 ml), stirred under room temperature for 2 h, concentrated under reduced pressure, and separated by silica gel column chromatography (ethyl acetate) to give compound 2 (1.1 g, yield 82%). Melting point 203-205° C. MS (ESI, M+1): 496.

Synthesis of Coupling Precursor 3-1 (u=2)—Synthesis Protocol:

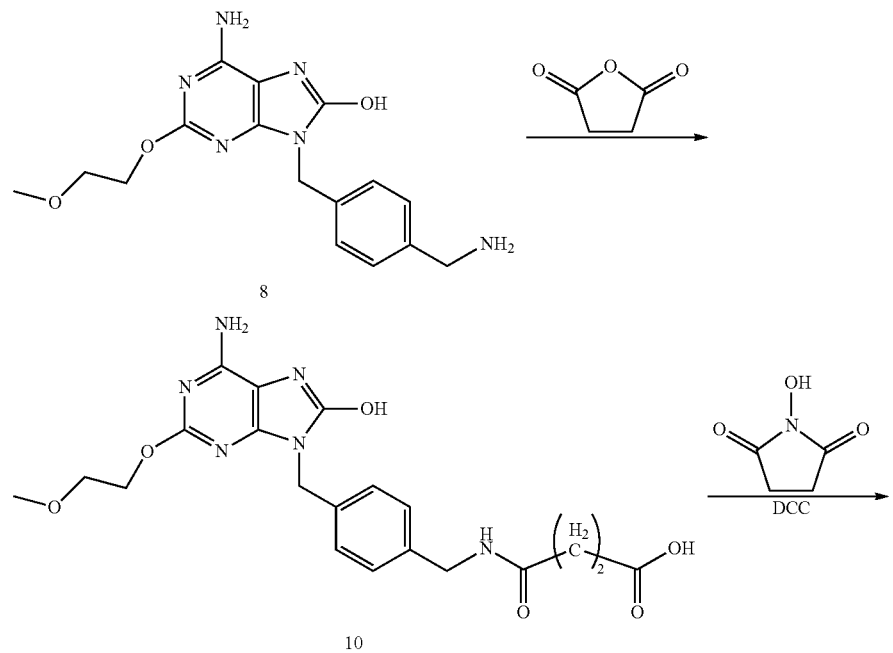

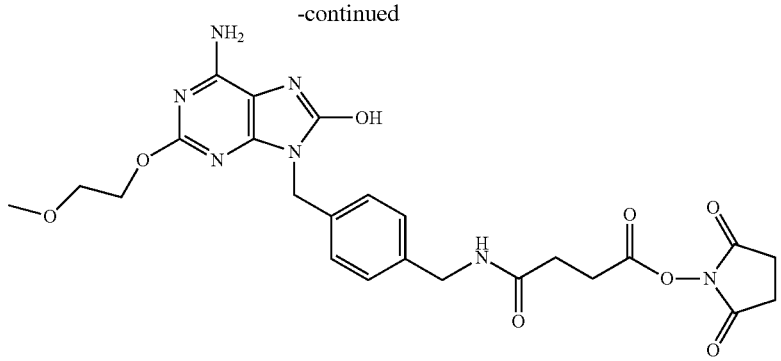

3-1

Synthesis Process: Compound 8 (1 g) was mixed with succinic anhydride (0.3 g) in DMF (50 ml) and stirred at room temperature for 12 h. N-hydroxy succinimide (0.34 g) and equal molar DCC were added. The mixture was stirred at room temperature for another 12 h to give a solution of compound 3 in DMF. The solution was distilled under reduced pressure to dryness. The resultant solid residue was extracted with ethyl acetate (50 ml), and then equal volume of diethyl ether was added. The mixture was frozen at −10° C. for 12 h and precipitated to give a solid 3 (u=2) (0.6 g, yield 38%). MS (ESI, M+1): 542.

Synthesis of Coupling Precursor 4-1—Synthesis Protocol

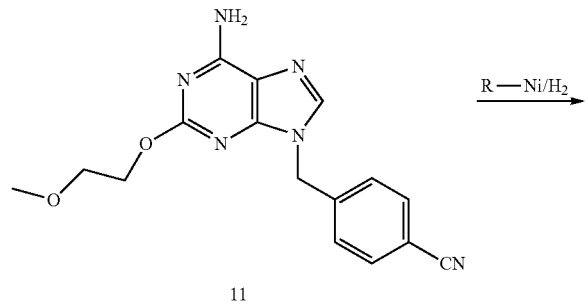

11

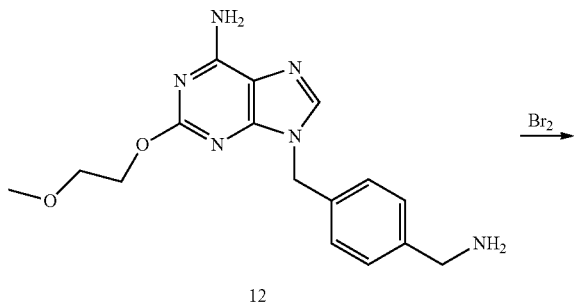

12

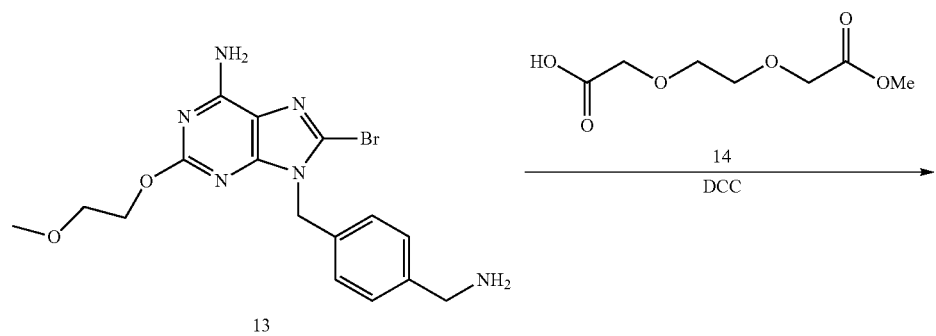

13

-continued

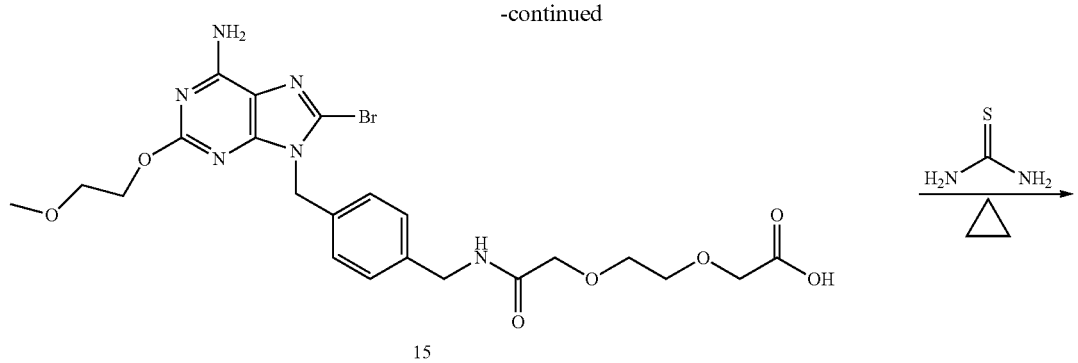

15

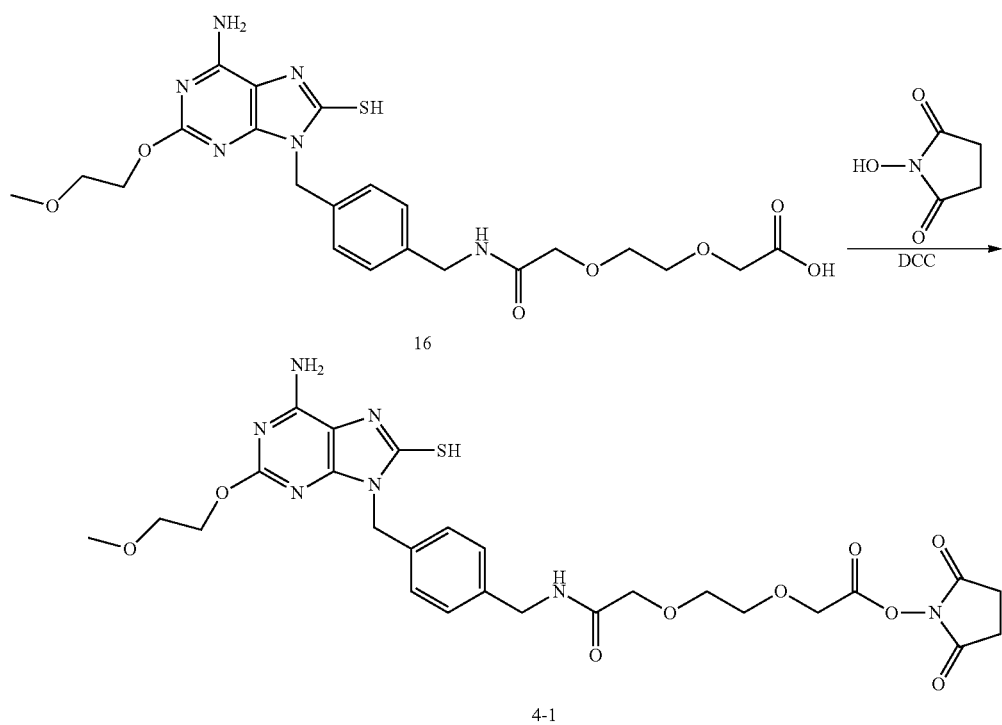

16

4-1

Note: 1) regioselective, scale up; 2) regioselective, scale up; 3) scale up, reactants: 3, reagents: 3, solvents: 3, steps: 3, stages: 3.

Synthesis of compound 12: the synthesis protocol is analogous to the synthesis of compound 8, yield: 88%, MS (ESI, M+1): 329.

Synthesis of compound 13: Compound 12 (1 g) was dissolved into dichloromethane (50 ml). Then bromine (10 ml) was added and the mixture was stirred at room temperature for 12 h. Air was blown through the mixture such that the excessive bromine was removed and absorbed into saturated sodium bicarbonate solution. The solid residue was filtered to give a pale yellow solid 13 (1 g), with a yield of 85% and mass spectra (ESI, M+1): 407.

Synthesis of compound 15: Compound 13 (0.5 g) was dissolved into anhydrous DMF (10 ml) and compound 14 (0.24 g) was added. The mixture was stirred homogenously, and then added with DCC (0.26 g) at 0° C. The mixture was stirred at 0° C. for 2 h and then at room temperature for another 12 h. DCU was filtered off and the remaining solution was distilled under reduced pressure to dryness. To The reference for synthesis of compound 11: PCT patent application No. 2011134669, published on Nov. 3, 2011.

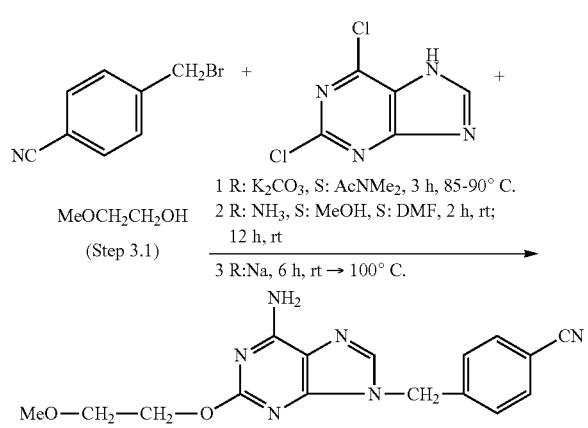

1 R: K₂CO₃, S: AcNMe₂, 3 h, 85-90° C.
2 R: NH₃, S: MeOH, S: DMF, 2 h, rt; 12 h, rt
3 R:Na, 6 h, rt → 100° C.

the residue was added 50 ml of saturated sodium bicarbonate solution. The mixture was stirred at 40° C. for 4 h. Under cooling, the mixture was adjusted to pH 4 with concentrated hydrochloric acid. The precipitated solid was filtered, washed with water, and dried to give compound 15 (0.5 g, yield 72%). MS (ESI, M+1):567.

Synthesis of compound 16: Compound 15 (0.4 g) was dissolved into methanol (20 ml), and thiourea (1 g) was added. The mixture was heated under reflux for 12 h, cooled and filtered. The filtrate was concentrated under reduced pressure and the residue was dissolved into 5% sodium carbonate solution (10 ml). Under cooling, the mixture was adjusted to pH 4 with concentrated hydrochloric acid. The precipitated solid was filtered, washed with water and dried to give compound 16 (0.23 g, yield 65%). MS (ESI, M+1): 521.

Synthesis of coupling precursor 4: Compound 16 (0.15 g) was dissolved into anhydrous DMF (5 ml), and N-hydroxy succinimide (0.04 g) was added. The mixture was stirred homogenously and then added with DCC (0.06 g) at 0° C. The resultant mixture was stirred at 0° C. for 2 h and then at room temperature for another 12 h. DCU was filtered off and the filtrate was distilled under reduced pressure to dryness. The remaining solid was extracted with ethyl acetate (10 ml). To the extraction was added equal volume of diethyl ether. The mixture was frozen at −10° C. for 12 h and precipitated to give a solid 4 (0.05 g, yield 32%). MS (ESI, M+1):618.

For immune therapy and immunomodulation of malignant tumor, the immune receptor modifier conjugate may be administered by intraperitoneal, subcutaneous, intramuscular or intravenous injection. Alternatively, the immune receptor modifier conjugate may be administered by in vivo re-transfusing the isolated immune cells after co-culturing the immune cells (for example, dendritic cells, natural killer (NK) cells, lymphocyte, monocyte/macrophage, granulocyte, etc.) with the immune receptor modifier conjugate of this invention.

The immune receptor modifier conjugate of the present invention can be used for immunomodulation, antibody preparation, anti-virus, diabetes, tumor immunomodulation and tumor biological-immunotherapy. The above-mentioned conjugates or salts thereof can be formulated into therapeutic drugs suitable for such therapies, or formulated into compound drugs with other pharmaceuticals, or formulated into complexes or combinations with pharmaceutically acceptable carriers. The present immune receptor modifier conjugates or salts thereof can be present at various ratios in the therapeutic preparations.

BRIEF DESCRIPTION OF THE DRAWINGS

The present invention is further illustrated by the following figures and specific examples.

In the figures.

DETAILED DESCRIPTION OF THE INVENTION

Figure 1:
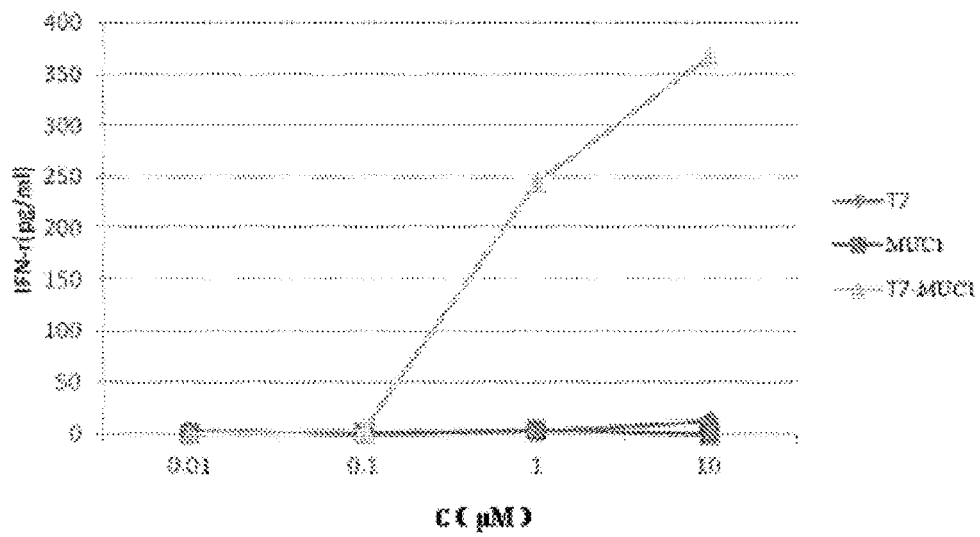
FIG. 1 is a graph showing the comparison of IFN-γ induction by conjugate 5-4, in which T7 is coupling precursor 1 and T7-MUC1 is conjugate 1-2.

Source of the antigens: the molecular weight of all proteins may be found in the international protein database (http://www.uniprot.org/uniprot/P48432).

Source of proteins or polypeptides: Except the proteins or polypeptides for which the specific preparation or synthesis methods have been described, other polypeptides are synthesized by Hybio Pharmaceutical Co., Ltd.

Proteins are purchased from or synthesized by the following companies:

GenScript Inc., Nanjing, China (http://www.genscript.com.cn/index.html);

Novoprotein Scientific Inc., Shanghai, China (http://www.sinobio.net/);

Sino Biological Inc., Beijing, China (http://www.sinobiological.cn/);

Abnova Corporation (http://www.abnova.com/cn/).

Mass spectrometer for material identification: LDI-1700 MALDI-TOF mass spectroscopy (Linear Scientific Inc., USA).

The method for determining coupling degree by mass-spectrometry is, for example, as follows:

The average molecular weight of POSTN is 86 kDa (see, *World J Gastroenterol*, 2007 Oct. 21; 13(39); 5261-5266; http://www.sinobiological.cn/Periostin-Protein-g-465.html). The molecular weight of the resultant coupling product 5-6 is 88132, as determined by mass spectrum. The coupling degree is calculated as follows: (88132-86000)/427=4.99≈5 (the molecular weight 427 is obtained by subtracting one $H_2O$ molecular from molecular weight of compound 3). Thus, it can be determined that 5 monomers of compound 3 were coupled (coupling degree m=5).

The preparation of the present coupling conjugate is further illustrated by the following examples.

Synthesis of Compound 1-1:

MG7 (0.37 mmol) and compound 1 (0.88 mmol) were mixed and dissolved into absolute methanol, and then anhydrous triethylamine (1.12 mmol) was added. The mixture was reacted at 45° C. for 4 h. The solvent was removed by evaporating under reduced pressure and the residue was separated by silica gel column chromatography (10% methanol-dichloromethane) to give compound 1-1 (55 mg, yield 23%). MS (ESI): theoretical m/z 969.1516, found 970.1518 (M+H).

Synthesis of Compound 1-2:

Analogous to the synthesis of compound 1-1, MUC1 (epitope) was mixed with compound 1 at a molar ratio of 1:1, and then 1.5-fold molar of triethylamine was added. The resultant mixture was allowed to react in methanol at 20° C.

for 12 h. For work up, please refer to "Synthesis of compound 1-1". This gave compound 1-2 (yield 20%). MS (ESI): theoretical m/z 3341.72, found 3342.75 (M+H).

Synthesis of Compound 1-3:

Analogous to the synthesis of compound 1-1, M2e was mixed with compound 1 at a molar ratio of 1:1, and then 1.5-fold molar of triethylamine was added. The resultant mixture was allowed to in methanol at 20° C. for 12 h. For work up, please refer to "Synthesis of compound 1-1". This gave compound 1-3 (yield 25%). MS (ESI): theoretical m/z 3303.32, found 3304.33 (M+H).

Synthesis of Compound 2-1:

Compound 2 (0.22 mmol) was mixed with M2e (0.1 mmol) in anhydrous DMSO (10 ml). The mixture was stirred at room temperature for 12 h. To the mixture $H_2O$ (100 ml) was added. The resultant mixture was lyophilized to remove solvents and the residue was separated by silica gel column chromatography (10% methanol-dichloromethane) to give compound 2-1 (56 mg, yield 15%). MS (ESI): theoretical m/z 3761.71, found 3761.75 (M+H).

Synthesis of Compound 5:

1) The expression and preparation of OCT4 are described in *Progress in Modern Biomedicine*, Vol. 10, NO. 9, May, 2010, 1610-1612).

2) Synthesis of Compound 5 (m=5):

OCT4 (10 mg, average molecular weight: 38216) was dissolved into PBS solution (10 ml). A solution of compound 3 (u=2, 50 mg) in 2 ml DMSO was mixed with equimolar NHS, and then equimolar EDC was added. The mixture was stirred at room temperature for 2 h. Subsequently, the solution of OCT 4 in PBS was added and the resultant mixture was stirred overnight at 10° C. The mixture was separated with PD-10 desalting column (Amersham disposable PD-1 desalting column). The eluates containing conjugate 5 were combined (detected by the absorptance at 320 nm) and lyophilized. The average molecular weight was 40348, as determined by MS. Thus, it was determined that the product 5 comprises five monomers of compound 3 (u=2), i.e. coupling degree m=5. Compound 5 (m=1, 2, 3, 4) was synthesized with compound 3 (u=2) at different molar ratios by the same method.

Synthesis of Compound 5-4:

1) Methods for preparing MUC1 (epitope) may be found in the references, such as, *Proc Natl Acad Sci*. 2011, 109(1): 261-266; *Angew Chem Int Ed Engl*, 2010, 49(21): 3688-3692; *Angew Chem Int Ed Engl*, 2011, 50(7): 1635-1639; *European Journal of Organic Chemistry*, 2011, 20(21): 3685-3689; and *Chemistry*, 2011, 17(23): 6396-6406.

According to compound 11 shown in the reference *Proc Natl Acad Sci*. 2011, 109(1): 261-266, the molecular weight of MUC1 (epitope) is 2967.

2) Coupling precursor 3 (u=2, 10 mg, 0.019 mmol) was dissolved into DMSO (2 ml) and MUC1 (epitope) (59 mg, 0.02 mmol) was added. The mixture was stirred at room temperature for 2 h, and then $H_2O$ (20 ml) was added. The solvent was removed by lyophilization and the residue was separated by silica gel column chromatography (10% methanol-dichloromethane) to give compound 5-4 (16 mg, yield 25%). MS (ESI): 3396.6 (M+H). Coupling degree m=1.

Synthesis of Compound 5-14:

Analogous to the synthesis of compound 5-4, except that MUC1 (epitope) was replaced by $NP_{366-374}$ (ASNENM-DAM), other solvents and reactants are used in identical molar ratios to give compound 5-14, MS (ESI): 1424.54 (M+H). Coupling degree m=1.

Synthesis of the Following Conjugates:

If the antigen is a protein, the synthesis is analogous to the synthesis of compound 5. If the antigen is a polypeptide (with the number of amino acids being less than 50), then follow the synthesis method of compound 5-4 (the solvents and reactants were in identical molar ratios, and the determination of reaction time, temperature, molecular weight and coupling degree, as well as the steps and conditions of the method were also identical). The conjugates obtained are shown in the table below.

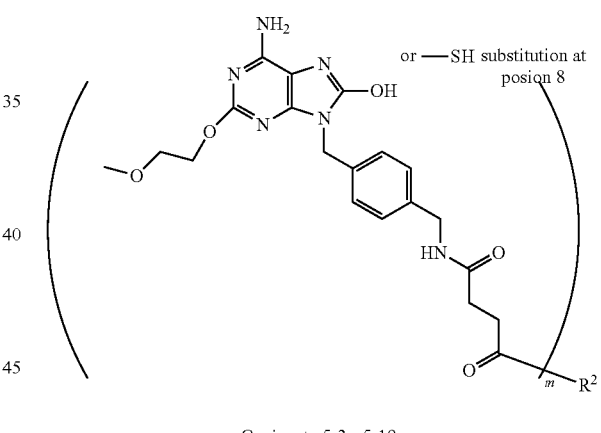

Conjugate 5-3 - 5-19

Wherein $R^2$ represents polypeptide or protein

| $R^2$ | NANOG | MUC1 (epitope) | MG7 | POSTN | Twist | Anxa1 | Akt1 | CD47 | Sp17 |
|---|---|---|---|---|---|---|---|---|---|
| Conjugate | 5-3 | 5-4 | 5-5 | 5-6 | 5-7 | 5-8 | 5-9 | 5-10 | 5-11 |
| Molecular weight | 36326 | 3396 | 1272 | 88132 | 22233 | 40420 | 50724 | 36067 | 18259 |
| Coupling degree | 4 | 1 | 1 | 5 | 3 | 4 | 6 | 2 | 2 |

| $R^2$ | PSMA | M2e | $NP_{366-374}$ | SGLT2 | PEAK1 | HER2 | MMP-10 | PD-L1 | PD-1 |
|---|---|---|---|---|---|---|---|---|---|
| Conjugate | 5-12 | 5-13 | 5-14 | 5-15 | 5-16 | 5-17 | 5-18 | 5-19 | 5-20 |
| Molecular weight | 86890 | 3357 | 1424 | 75029 | 194385 | 140469 | 55430 | 35834 | 33353 |
| Coupling degree | 6 | 1 | 1 | 5 | 3 | 6 | 3 | 6 | 4 |

Preparation of Conjungate 6:

1) SOX2 is prepared according to *Journal of Huazhong Normal University* (*Nat. Sci.*), 2008, 42 (1), 102-105. Sp17 is prepared according to *Chinese Journal of Pathophysiology*, 2001, 17(10), 1019-1021. PSMA is prepared according to *The Journal of Biomedical Research* (*Natural Science*), 2010, 30(11): 1608-1611.

2) Synthesis of Compound 6 (m=3):

SOX2 (10 mg, average molecular weight: 34310) was dissolved into PBS solution (10 ml). A solution of compound 4 (50 mg) (PEG=ethylene glycol group) in DMSO (2 ml) was mixed with equimolar NHS, and then equimolar EDC was added. The mixture was stirred at room temperature for 2 h. Subsequently, the solution of SOX2 in PBS was added and the resultant mixture was stirred overnight at 10° C. The mixture was separated on PD-10 desalting column (Amersham disposable PD-1 desalting column). The eluates containing compound 6 (detected by the absorptance at 320 nm) were combined and lyophilized. The average molecular weight was 35817, as determined by MS. Thus, it was determined that the product 6 comprises three monomers of compound 4 (PEG=ethylene glycol group), i.e. coupling degree m=3. Compound 6 (m=1, 2, 4) was synthesized with compound 4 (PEG=ethylene glycol group) used at different molar ratios by the same method.

Synthesis of Compound 6-3 (m=4):

Synthesis of compound 6-3 (m=4) was analogous to the synthesis of compound 6. The molecular weight of NANOG was 34620. Compound 6-3 (m=4) was analyzed to have a molecular weight of 36630.24. Compound 6-3 (m=1, 2, 3, 5) was synthesized with compound 4 (PEG=ethylene glycol group) at different molar ratios by the same method.

Synthesis of Compound 6-14 (the Ligand in General Formula I is $NP_{366-374}$, n=3):

Compound 4 (PEG=ethylene glycol group) (11 mg, 0.02 mmol) was dissolved into DMSO (2 ml), and then $NP_{366-374}$ trimer (59.1 mg, 0.02 mmol) was added. The mixture was stirred at room temperature for 2 h. To the mixture with 20 ml water was added. The resultant mixture was lyophilized to remove solvents, and then the residue was separated by silica gel column chromatography (10% methanol-dichloromethane) to give compound 6-14 (in which $R^2$ is $NP_{366-374}$ trimer) (17 mg, yield 25%). MS (ESI): 3460.8 (M+H). Coupling degree m=1.

Synthesis of the Following Conjugates:

If the antigen is a protein, synthesis is analogous to the synthesis of compound 6. If the antigen is a polypeptide (with the number of amino acids being less than 50), then follow the synthesis process of compound 6-14 (the solvents and reactants were in identical molar ratios, and the determination of reaction time, temperature, molecular weight and coupling degree, as well as the steps and conditions of the method were also identical). The conjugates obtained are shown in the table below.

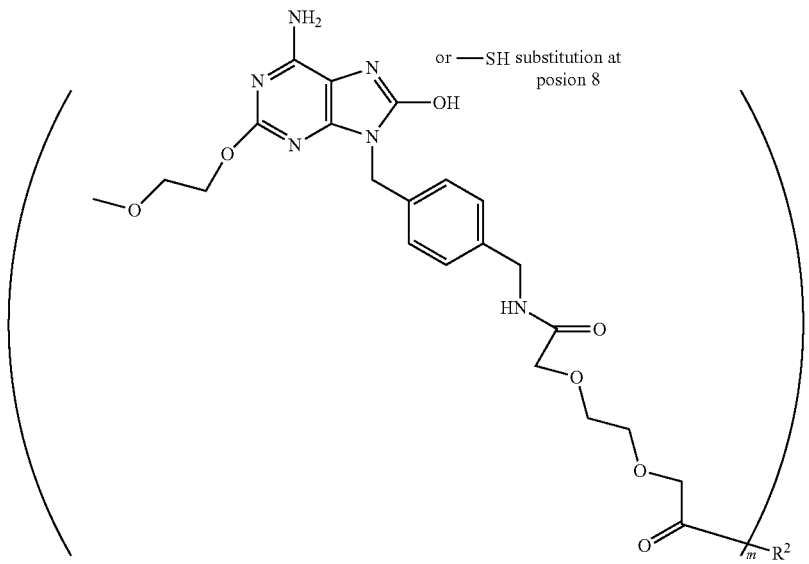

Conjugate 6-3 - 6-19

$R^2$ represents polypeptide or protein

| $R^2$ | NANOG | MUC1 (epitope) | MG7 | POSTN | Twist | Anxa1 | Akt1 | CD47 | Sp17 |
|---|---|---|---|---|---|---|---|---|---|
| Conjugate | 6-3 | 6-4 | 6-5 | 6-6 | 6-7 | 6-8 | 6-9 | 6-10 | 6-11 |
| Molecular weight | 36630 | 3469 | 2257 | 88512 | 22461 | 40724 | 51362 | 36219 | 18411 |
| Coupling degree | 4 | 1 | 1 | 5 | 3 | 4 | 6 | 2 | 2 |

-continued

| $R^2$ | PSMA | M2e | $NP_{366-374}$ | SGLT2 | PEAK1 | HER2 | MMP-10 | PD-L1 | PD-1 |
|---|---|---|---|---|---|---|---|---|---|
| Conjugate | 6-12 | 6-13 | 6-14 | 6-15 | 6-16 | 6-17 | 6-18 | 6-19 | 6-20 |
| Molecular weight | 87346 | 3433 | 3460 | 75410 | 194614 | 140925 | 55659 | 36290 | 33657 |
| Coupling degree | 6 | 1 | 1 | 5 | 3 | 6 | 3 | 6 | 4 |

(Note:
$R^2$ of conjugate 6-14 is $NP_{366-374}$ trimer; and $R^2$ of conjugate 6-5 is MG7 trimer)

Figure 2:
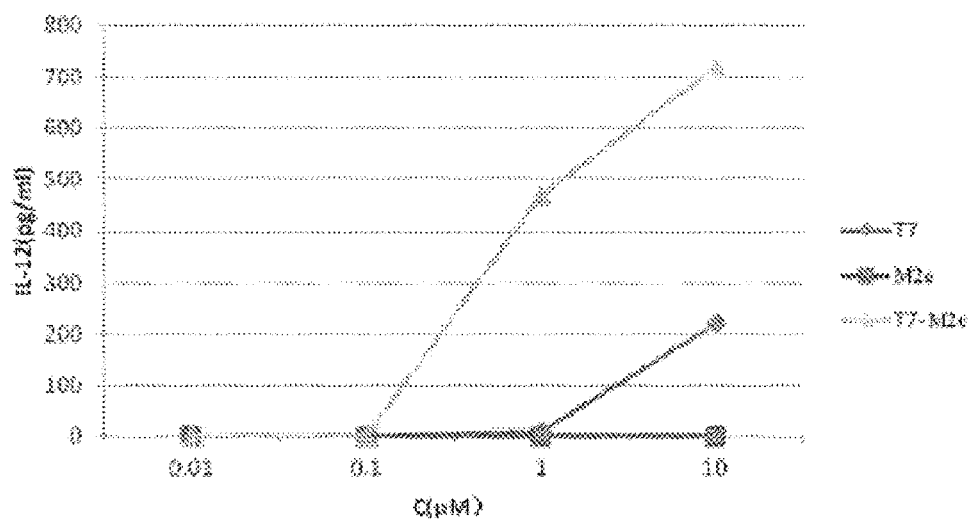
FIG. 2 is a graph showing the comparison of IL-12 induction by conjugate 2-1, in which T7 is coupling precursor 2 and T7-M2e is conjugate 2-1.

Method for Assaying Bioactivity
1. Method for Assaying Immune Factors:
Method: ELISA
Reagents and Conditions:
Human peripheral blood mononuclear cells were separated by centrifugation sedimentation. The centrifugator was Ficoll-Hypaque. The separated cells were suspended in RPMI1640 medium, and then 10% of FBS, L-glutamine, and penicillin/streptomycin (RP10, Invitrogen) were added. The resultant mixture was placed into 96-well plate. The cells were stimulated by the compounds of the present invention at a concentration of 0.1-10 μM, and cultured at 37° C. with 5% $CO_2$ for 24 h. The levels of γ-interferon and interleukin-12 were measured using Luminex (Austin, Tex.), FIGS. 1 and 2 showed the in vitro immunity-induction effects of conjugate 5-4 and conjugate 2-1, respectively. The results shown in the figures were average of three separate experiments.

2. Method for Assaying Anti-Tumor Effect:
The method for assaying in vivo anti-tumor effect by the conjugates of this application such as conjugate 5-4 in mice was as follows:
Cell: 4T1, mouse breast carcinoma cells, $1 \times 10^6$ cells/mouse.
Animals: 5-week-old BALB/C mice (the number of male mice is identical with female mice).
Tumor transplantation: Tumor cells were injected subcutaneously on left/right sides of a mouse.
Administration: Intraperitoneal injection (0.125 mg/mouse/injection, PBS solution). Drugs were administered three times in total: one week before transplantation, on the day of transplantation and 7 days after transplantation.

Figure 3:
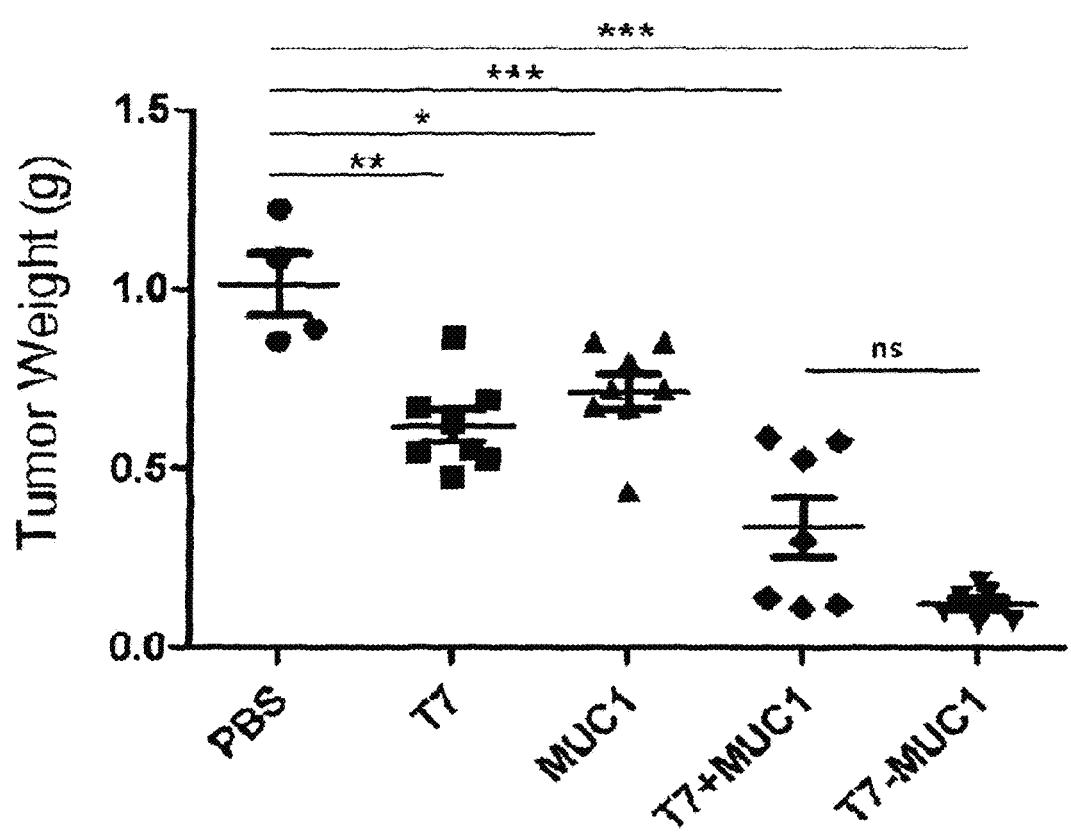
FIG. 3 is a diagram schematically showing the tumor-inhibiting effects of conjugate 5-4 (m=1), in which T7 is coupling precursor 10 and T7-MUC1 is conjugate 5-4 (m=1), *p<0.001.
Figure 4:
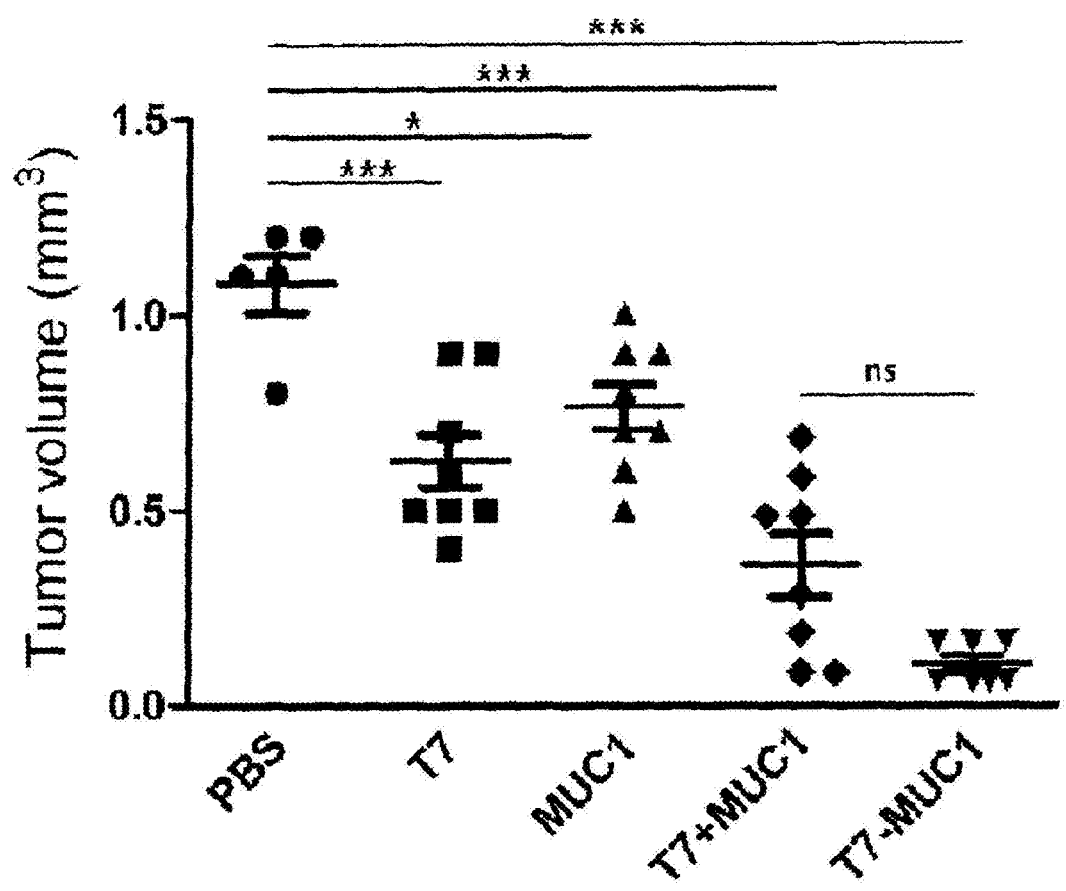
FIG. 4 is a diagram schematically showing the tumor-inhibiting effects of conjugate 5-4 (m=1), in which T7 is coupling precursor 10 and T7-MUC1 is conjugate 5-4 (m=1), *p<0.001.
Figure 5:
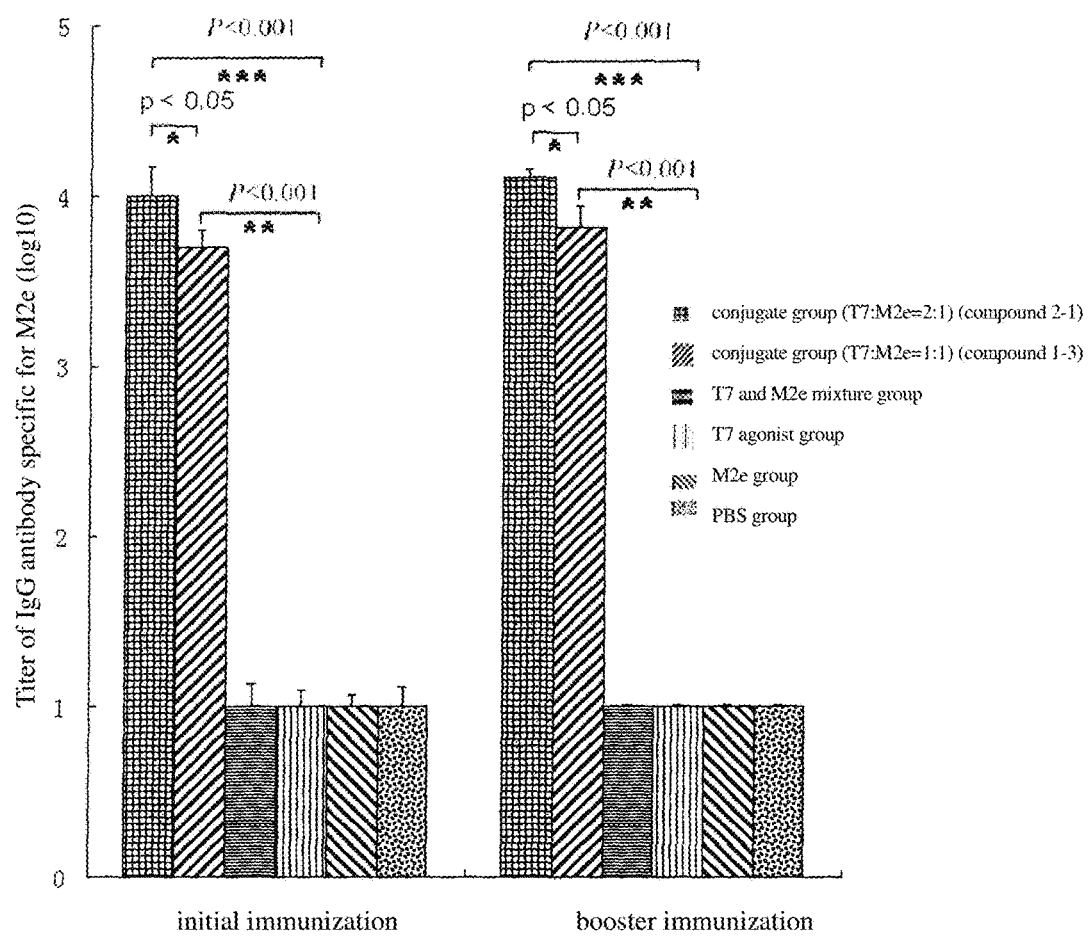
FIG. 5 is a diagram schematically showing the in vivo antibody-inducing effect of the influenza virus conserved protein M2e conjugate (T7-M2e), compared with original antigen M2e.
Figure 6:
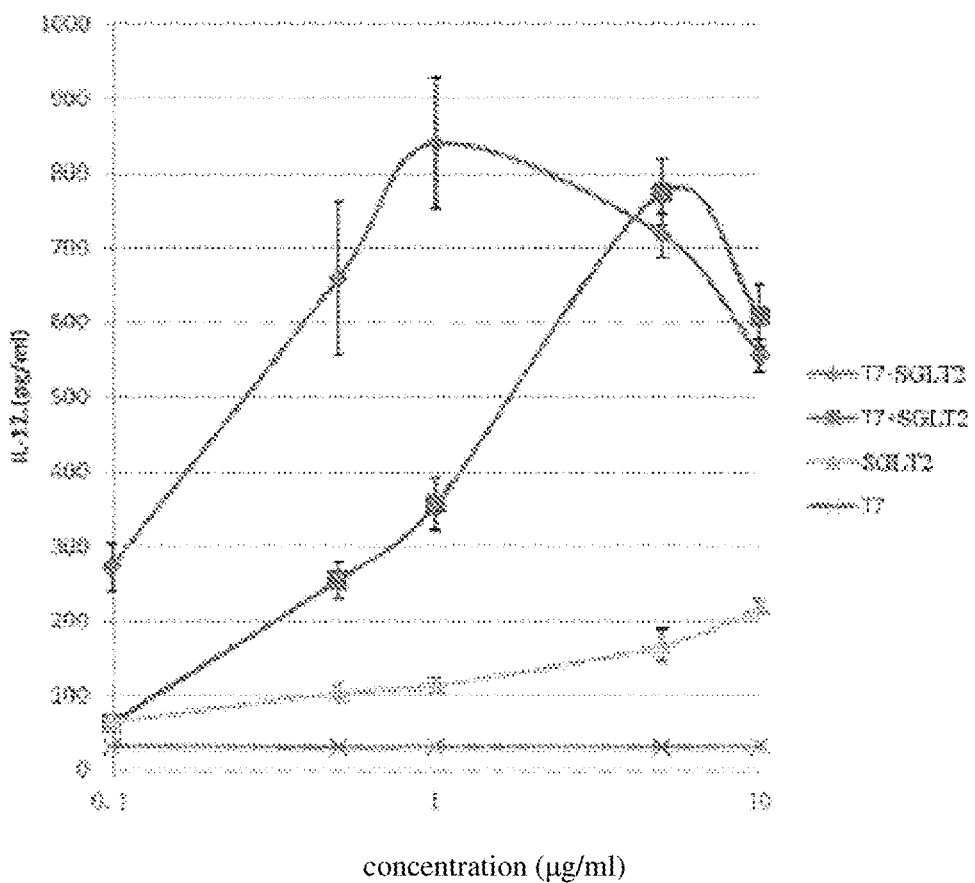
FIG. 6 is a diagram schematically showing the immune-induction effect of urine glucose reabsorption functional protein SGLT2, in which T7-SGLT2 is conjugate 5-15.

The health state and tumor size of the mice were monitored (via visual observation). After 14 days, the mice were killed. Blood samples were collected from each mouse for testing cytokines, and the tumors were taken out to measure the weight, length and width so as to calculate their volumes. The method used for testing in vivo anti-tumor effect by, for example, compound 6-17, in mice was the same as those described above, except that the cells used were mouse lung carcinoma cells. FIGS. 3 and 4 showed the tumor-inhibiting effects. FIG. 5 showed the antibody induction effect. FIG. 6 showed immunity-induction effect of diabetes-related proteins.

3. Antibody Induction Method (Taking Compounds 1-3 and 2-1 as the Examples):
36 female BALB/c mice (5 to 6-week-old, about 16 g) were randomly assigned into six cages, 6 mice each. The mice were provided with standard diet prepared by animal center and cooled boiled water on daily basis. After purchase, the mice were fed for one week to adapt the environment. After health examination, the experiments were started. The experimental animals were randomly divided into six groups, as shown in Table 4:

TABLE 4

Grouping and treatment of experimental animals

| Group | Immune dose (per mouse) |
|---|---|
| PBS group | 200 μL sterile PBS |
| TLR-7 agonist group | 18 μM TLR-7 agonist |
| M2e group | 18 μM M2e antigen |
| TLR-7 and M2e mixture group | 200 μL mixture (18 μM TLR-7 and M2e, mixed at a ratio 1:1 by volume) |
| Conjugate (TLR-7:M2e = 1:1) group | 18 μM conjugate (TLR-7:M2e = 1:1) (conjugate 1-3) |
| Conjugate (TLR-7:M2e = 2:1) group | 18 μM conjugate (TLR-7:M2e = 2:1) (conjugate 2-1) |

200 μl of the drugs were administered intraperitoneally to the above groups of mice, respectively. Booster immunization was performed with the same antigen and dosage on day 14 after initial immunization. Blood samples were collected by cutting rat tail for three times: before initial immunization, before booster immunization and 7 days after booster immunization. The blood samples were placed into 1.5 ml Eppendorf tubes at 4° C. for several hours, and then centrifuged at 3000 rpm for 15 min to separate serum. M2e-specific antibodies in the immune serum were assayed using standard ELISA method.

The invention claimed is:
1. An immune receptor modifier conjugate, wherein the conjugate is obtained by the reaction between a coupling precursor and a biotic ligand, and is a compound of formula (I):

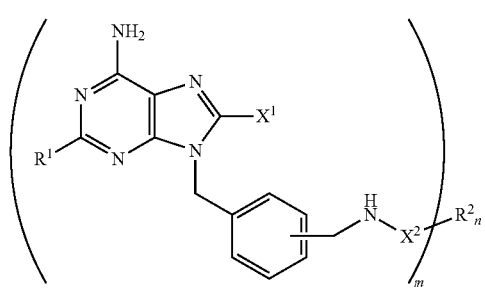

wherein $R^2$ is the biotic ligand, $X^1$ is OH or SH, $R^1$ is linear alkyl, branched alkyl, substituted alkyl, unsubstituted alkyl or alkoxyalkyl, $X^2$ is

or

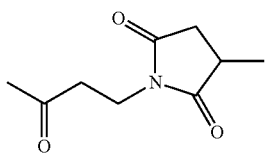

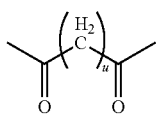

or

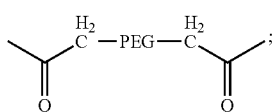

and m and n each are an integer selected from 1 to 10;

When the coupling precursor is a compound of formula 1:

1

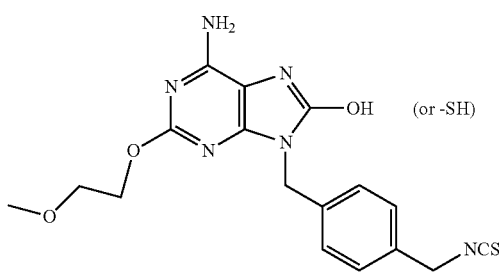

$X^2$ is the group thiocarbonyl

When the coupling precursor is a compound of formula 2:

2

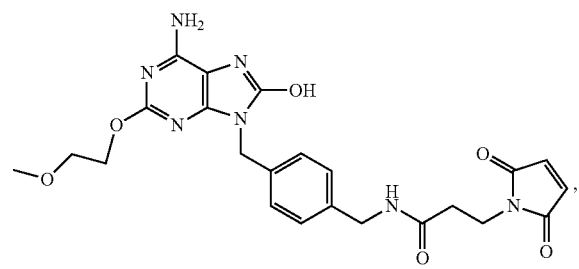

$X^2$ is the group

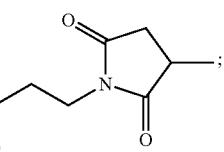

When the coupling precursor is a compound of formula 3:

3

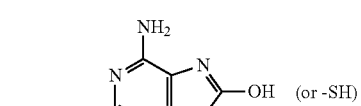

$X^2$ is the group

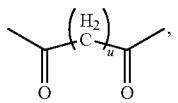

in which u is an integer selected from 0 to 12; or

When the coupling precursor is a compound of formula 4:

4

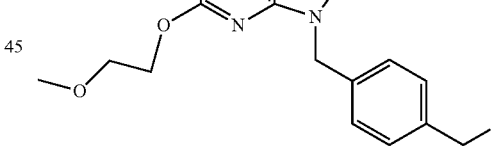

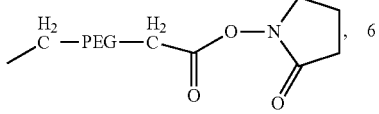

$X^2$ is the group

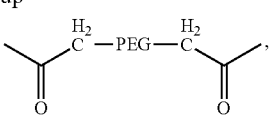

in which PEG is a polyethylene glycol group.

2. The immune receptor modifier conjugate of claim 1, wherein the biotic ligand is one or more selected from the group consisting of polypeptide, protein, glycoprotein, polysaccharide, polynucleotide, inactivated cells and inactivated microorganisms.
3. The immune receptor modifier conjugate of claim 1, wherein the conjugate comprises the compounds of formulae 1-1, 1-2, 1-3 and 2-1:
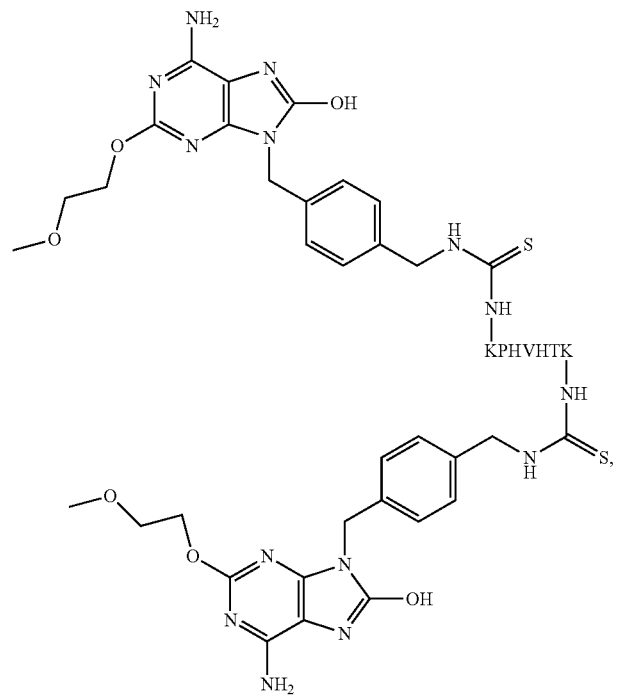
1-1
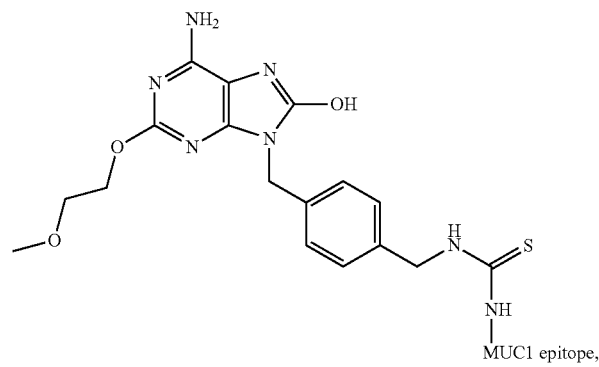
1-2
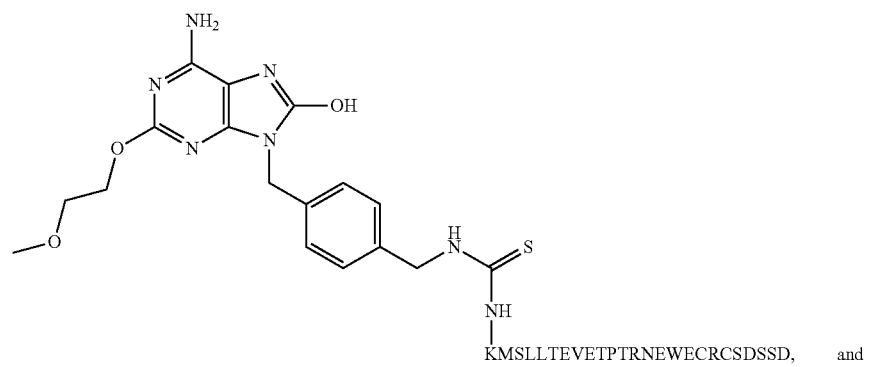
1-3

-continued
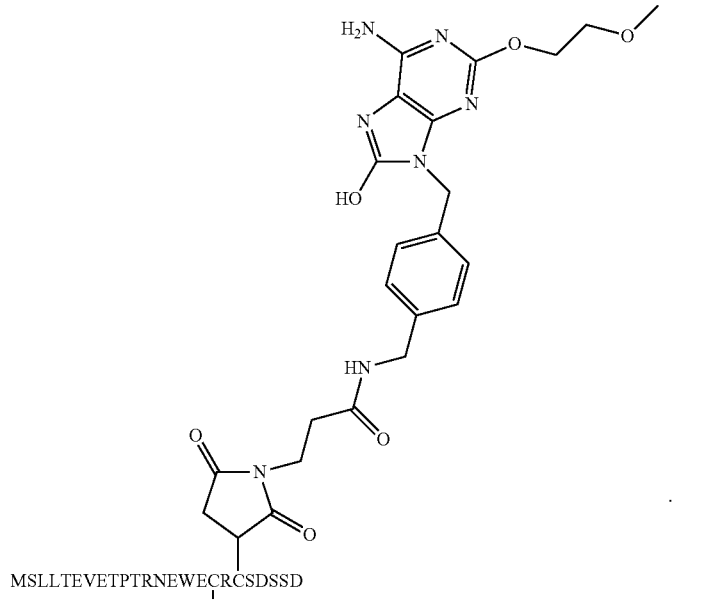
2-1
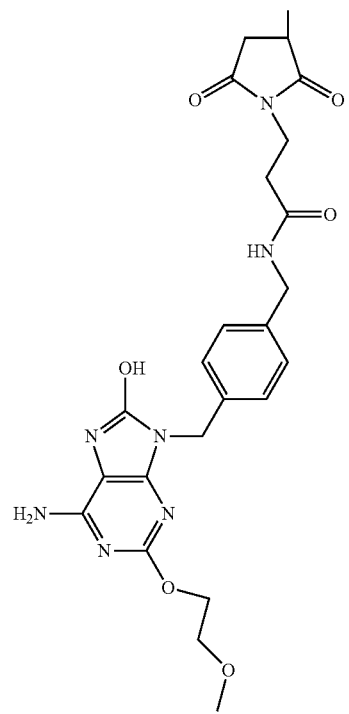

4. The immune receptor modifier conjugate of claim 1, wherein the conjugate comprises:

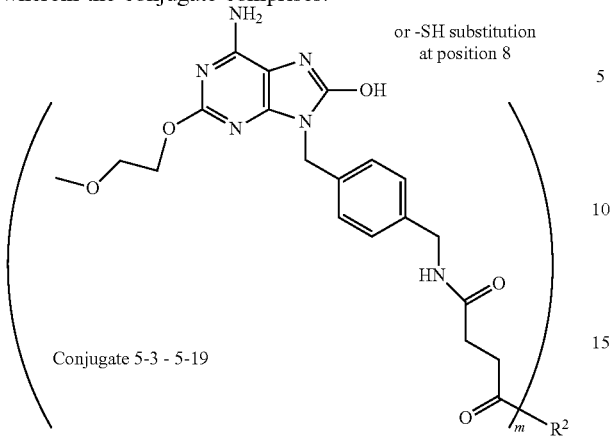

Conjugate 5-3 - 5-19 or -SH substitution at position 8 wherein the biotic ligand $R^2$ is polypeptide or protein;

| $R^2$ | NANOG | MUC1 (epitope) | MG7 | POSTN | Twist | Anxa1 | Akt1 | CD47 | Sp17 |
|---|---|---|---|---|---|---|---|---|---|
| Conjugate | 5-3 | 5-4 | 5-5 | 5-6 | 5-7 | 5-8 | 5-9 | 5-10 | 5-11 |
| Molecular weight | 36326 | 3396 | 1272 | 88132 | 22233 | 40420 | 50724 | 36067 | 18259 |
| Coupling degree | 4 | 1 | 1 | 5 | 3 | 4 | 6 | 2 | 2 |

| $R^2$ | PSMA | M2e | $NP_{366-374}$ | SGLT2 | PEAK1 | HER2 | MMP-10 | PD-L1 | PD-1 |
|---|---|---|---|---|---|---|---|---|---|
| Conjugate | 5-12 | 5-13 | 5-14 | 5-15 | 5-16 | 5-17 | 5-18 | 5-19 | 5-20 |
| Molecular weight | 86890 | 3357 | 1424 | 75029 | 194385 | 140469 | 55430 | 35834 | 33353 |
| Coupling degree. | 6 | 1 | 1 | 5 | 3 | 6 | 3 | 6 | 4. |

5. The immune receptor modifier conjugate of claim 2, wherein the conjugate comprises the compounds of formulae 1-1, 1-2, 1-3 and 2-1:

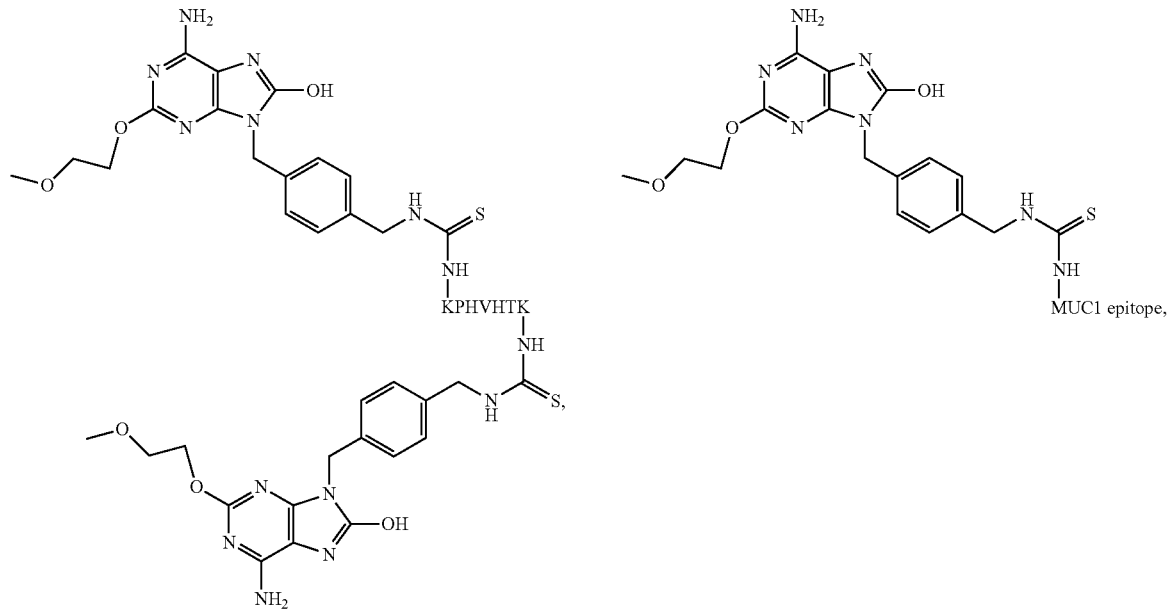

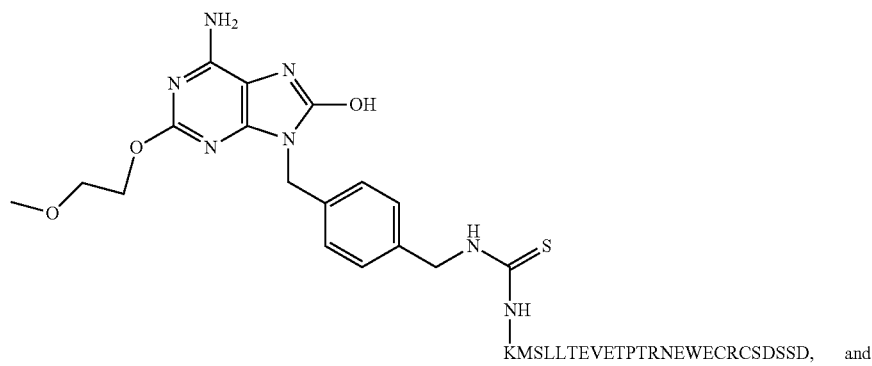
KMSLLTEVETPTRNEWECRCSDSSD, and
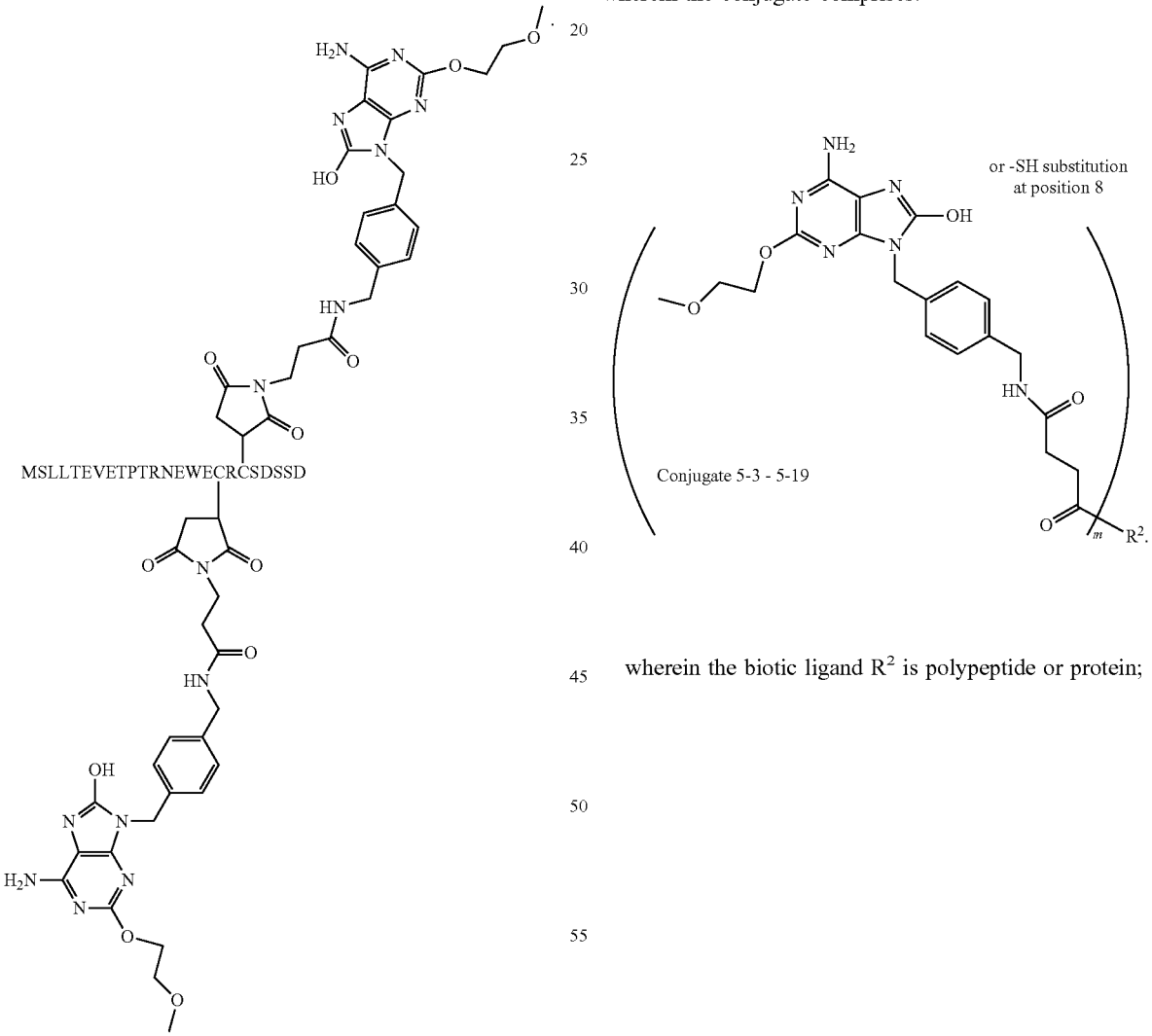
6. The immune receptor modifier conjugate of claim 2, wherein the conjugate comprises:
Conjugate 5-3 - 5-19
or -SH substitution at position 8
wherein the biotic ligand $R^2$ is polypeptide or protein;
| $R^2$ | NANOG | MUC1 (epitope) | MG7 | POSTN | Twist | Anxa1 | Akt1 | CD47 | Sp17 |
|---|---|---|---|---|---|---|---|---|---|
| Conjugate | 5-3 | 5-4 | 5-5 | 5-6 | 5-7 | 5-8 | 5-9 | 5-10 | 5-11 |
| Molecular weight | 36326 | 3396 | 1272 | 88132 | 22233 | 40420 | 50724 | 36067 | 18259 |

-continued
| | | | | | | | MMP- | | |
|---|---|---|---|---|---|---|---|---|---|
| Coupling degree | 4 | 1 | 1 | 5 | 3 | 4 | 6 | 2 | 2 |
| $R^2$ | PSMA | M2e | $NP_{366-374}$ | SGLT2 | PEAK1 | HER2 | MMP-10 | PD-L1 | PD-1 |
| Conjugate | 5-12 | 5-13 | 5-14 | 5-15 | 5-16 | 5-17 | 5-18 | 5-19 | 5-20 |
| Molecular weight | 86890 | 3357 | 1424 | 75029 | 194385 | 140469 | 55430 | 35834 | 33353 |
| Coupling degree. | 6 | 1 | 1 | 5 | 3 | 6 | 3 | 6 | 4. |
7. The immune receptor modifier conjugate of claim 1, wherein the coupling precursor is a compound of formula 3, and wherein the coupling precursor is a synthesis reaction product of a compound of formula 10:
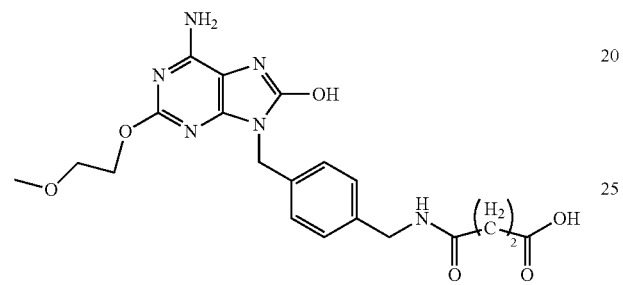
and
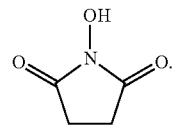
\* \* \* \* \*

UNITED STATES PATENT AND TRADEMARK OFFICE
CERTIFICATE OF CORRECTION

PATENT NO. : 10,030,066 B2
APPLICATION NO. : 14/434743
DATED : July 24, 2018
INVENTOR(S) : Guangyi Jin et al.

Page 1 of 1

It is certified that error appears in the above-identified patent and that said Letters Patent is hereby corrected as shown below:

On the Title Page

Under Foreign Application Priority Data, the application number for the Chinese application "2012 1 0382202" should be -- 201210382202.8 --.

In the Specification

Columns 15-16, Table 3, under heading "Antigen", fourth line of text (six instances) "Number of parents with" should be -- Number of patients with --.

Columns 15-16, Table 3, under Serial No. "19", the "Antigen" heading "Bet-abo" should be -- Bet-abi --.

Columns 15-16, Table 3, under Serial No. "42", the "Antigen" heading "Medothelin" should be -- Mesothelin --.

Columns 17-18, Table 3-continued, under heading "Antigen", fourth line of text (three instances) "Number of parents with" should be -- Number of patients with --.

Signed and Sealed this
Twenty-fifth Day of September, 2018

Andrei Iancu
*Director of the United States Patent and Trademark Office*